US012564480B2

(12) United States Patent
Hwang et al.

(10) Patent No.:  US 12,564,480 B2
(45) Date of Patent:        Mar. 3, 2026

(54) SMART DENTAL IMPLANT SYSTEM FOR AMBULATORY DENTAL CARE

(71) Applicants: THE TRUSTEES OF THE UNIVERSITY OF PENNSYLVANIA, Philadelphia, PA (US); TEMPLE UNIVERSITY—OF THE COMMONWEALTH SYSTEM OF HIGHER EDUCATION, Philadelphia, PA (US)

(72) Inventors: Geelsu Hwang, Wynnewood, PA (US); Hye-Eun Kim, Philadelphia, PA (US); Jonathan Korostoff, Philadelphia, PA (US); Albert Kim, Philadelphia, PA (US)

(73) Assignees: THE TRUSTEES OF THE UNIVERSITY OF PENNSYLVANIA, Philadelphia, PA (US); TEMPLE UNIVERSITY—OF THE COMMONWEALTH SYSTEM OF HIGHER EDUCATION, Philadelphia, PA (US)

( * ) Notice: Subject to any disclaimer, the term of this patent is extended or adjusted under 35 U.S.C. 154(b) by 515 days.

(21) Appl. No.: 18/064,747

(22) Filed: Dec. 12, 2022

(65) Prior Publication Data

US 2023/0107743 A1      Apr. 6, 2023

Related U.S. Application Data

(63) Continuation of application No. PCT/US2021/037223, filed on Jun. 14, 2021.

(Continued)

(51) Int. Cl.
*A61C 8/00*        (2006.01)
*A61C 8/02*        (2006.01)

(Continued)

(52) U.S. Cl.
CPC .......... *A61C 8/0006* (2013.01); *A61C 8/0012* (2013.01); *A61C 8/0068* (2013.01);
(Continued)

(58) Field of Classification Search
CPC ... A61C 8/0006; A61C 8/0012; A61C 8/0068; A61N 5/0601
See application file for complete search history.

(56) References Cited

U.S. PATENT DOCUMENTS 4,027,392  A  *   6/1977  Sawyer .................. A61C 19/00
                                                          433/32
4,549,547  A  *  10/1985  Brighton ................ A61N 1/372
                                                          607/51

(Continued)

OTHER PUBLICATIONS

Acosta et al., "BaTiO3-based piezoelectrics: Fundamentals, current status, and perspectives," Applied Physics Reviews 4(4):041305 (2017) 54 pgs.

(Continued)

*Primary Examiner* — Ralph A Lewis
(74) *Attorney, Agent, or Firm* — Baker Botts L.L.P.

(57) ABSTRACT

Smart dental implant systems and methods for ambulatory dental care are provided. In some embodiments, the disclosed subject matter includes a crown, adapted to mimic a patient's anatomy and location of the smart dental implant system. The crown can include piezoelectric nanoparticles, disposed on a surface of the crown and adapted to generate electricity from a patient's oral motion. In some embodiments, the disclosed subject matter includes an abutment, coupled to the crown. The abutment can include an energy harvesting circuit, operationally coupled to the piezoelectric nanoparticles and adapted to harvest the electricity, and a micro LED array, operationally coupled to the energy harvesting circuit and adapted to photobiomodulate surrounding peri-implant soft tissue.

20 Claims, 30 Drawing Sheets

US 12,564,480 B2

Page 2

Related U.S. Application Data

(60) Provisional application No. 63/038,494, filed on Jun. 12, 2020.

(51) Int. Cl.

| | |
|---|---|
| *A61L 27/10* | (2006.01) |
| *A61L 27/50* | (2006.01) |
| *A61N 5/06* | (2006.01) |
| *H02N 2/18* | (2006.01) |
| *H10N 30/85* | (2023.01) |

(52) U.S. Cl.

CPC .............. *A61L 27/10* (2013.01); *A61L 27/50* (2013.01); *A61N 5/0601* (2013.01); *H02N 2/181* (2013.01); *H02N 2/186* (2013.01); *H10N 30/852* (2023.02); *A61L 2400/12* (2013.01); *A61L 2430/12* (2013.01); *A61N 2005/0606* (2013.01); *A61N 2005/0652* (2013.01)

(56) References Cited

U.S. PATENT DOCUMENTS

| | | | | |
|---|---|---|---|---|
| 4,781,591 | A * | 11/1988 | Allen | A61B 8/00 607/51 |
| 5,292,252 | A * | 3/1994 | Nickerson | A61C 8/008 433/173 |
| 5,725,377 | A * | 3/1998 | Lemler | A61C 8/0007 433/201.1 |
| 9,327,115 | B2 * | 5/2016 | Neuman | A61N 2/02 |
| 9,776,014 | B2 * | 10/2017 | Neuman | A61C 13/0015 |
| 2006/0036253 | A1 * | 2/2006 | Leroux | A61B 17/70 623/23.57 |
| 2006/0265026 | A1 | 11/2006 | Madjar et al. | |
| 2010/0194333 | A1 | 8/2010 | Kassayan et al. | |
| 2012/0215281 | A1 * | 8/2012 | Neuman | A61N 2/02 607/51 |
| 2013/0300345 | A1 | 11/2013 | Trumbull et al. | |
| 2015/0134061 | A1 | 5/2015 | Friis et al. | |
| 2020/0009396 | A1 | 1/2020 | Huh et al. | |
| 2023/0107743 | A1 * | 4/2023 | Hwang | A61C 8/0068 433/29 |

OTHER PUBLICATIONS

Atieh et al., "The Frequency of peri-implant diseases: A Systematic Review and Meta-Analysis," J Periodontol 84(11):1586-1598 (2013).

Charalampakis et al., "Clinical and microbiological characteristics of peri-implantitis cases: A retrospective multicentre study," Clin Oral Implants Res 23(9):1045-1054 (2012).

Ciofani et al., "Barium titanate nanoparticles: Highly Cytocompatible dispersions in Glycol-Chitosan and Doxorubicin Complexes for Cancer Therapy," Nanoscale Research Letters 5(7):1093-1101 (2010).

Claffey et al., "Surgical treatment of peri-implantitis," J Clin Periodontol 35(Suppl. 8):316-332 (2008).

Daubert et al., "Prevalence and predictive factors for peri-implant disease and implant failure: A cross-sectional analysis," J Periodontol 86(3):337-347 (2015).

De Bortoli et al., "Ecological footprint of biomaterials for implant dentistry: Is the metal-free practice an eco-friendly shift?" J Clean Prod 213:723-732 (2019).

Elani et al., "Trends in dental implant use in the U.S., 1999-2016, and Projections to 2026," J Dent Res 97(13):1424-1430 (2018).

Esposito et al., "Treatment of peri-implantitis: What interventions are effective? A cochrane systematic review," Eur J Oral Implantol 5(Suppl):S21-S41 (2012).

Faggion Jr. et al., "Assessment of replication of research evidence from animals to humans in studies on peri-implantitis therapy," J Dentistry 37(10):737-747 (2009).

Figuero et al., "Management of peri-implant mucositis and peri-implantitis," Periodontol 2000 66(1):255-273 (2014).

Genchi et al., "Barium titanate nanoparticles: Promising multitasking vectors in nanomedicine," Nanotechnology 27(23):232001 (2016) 19 pgs.

Heintze et al., "Using a chewing simulator for fatigue testing of metal ceramic crowns," Journal of the Mechanical Behavior of Biomedical Materials 65:770-80 (2017).

Ikeda et al., "Difference in penetration of horseradish peroxidase tracer as a foreign substance into the peri-implant or junctional epithelium of rat gingivae," Clin Oral Implants Res 13(3):243-251 (2002).

International Search Report mailed Oct. 4, 2021 in International Application No. PCT/US21/37223.

Islam et al., "Ultrasonic Energy Harvesting Scheme for Implantable Active Stent," 2018 IEEE International Microwave Biomedical Conference (IMBioC) IEEE (2018) 3 pgs.

Jaffe, "Piezoelectric Ceramics," Journal of the American Ceramic Society 41(11):494-498 (1958).

Johannsen et al., "Dental implants from the patients perspective: Transition from tooth loss, through amputation to implants—negative and positive trajectories," J Clin Periodontol 39(7):681-687 (2012).

Kim et al., "An Implantable Pressure Sensing System with Electromechanical Interrogation Scheme," IEEE Transactions on Biomedical Engineering 61(7):2209-2217 (2014).

Kim et al., "An Universal Packaging Technique for Low-Drift Implantable Pressure Sensors," Biomed Microdevices 18(2):32 (2016) 18 pgs.

Kim et al., "Fabrication and characterization of 3D printed BaTiO3/PVDF nanocomposites," J Composite Mater 52(2):197-206 (2018).

Klinge et al., "Peri-implantitis," Dent Clin N Am 49(3):661-676 (2005).

Lee et al., "UP-Link: An Ultra-Low Power Implantable Wireless System for Long-Term Ambulatory Urodynamics," 2014 IEEE Biomedical Circuits And Systems Conference (BioCAS) Proceedings IEEE (2014) 4 pgs.

Lee et al., "When They are Not Listening: Harvesting Power from Idle Sensors in Embedded Systems," International Green Computing Conference IEEE (2014) 10 pgs.

Meyer et al., "Experimental mucositis and experimental gingivitis in persons aged 70 or over. Clinical and biological responses," Clin Oral Implants Res 28(8):1005-1012 (2017).

Nickenig et al., "Oral health-related quality of life in partially edentulous patients: Assessments before and after implant therapy," Journal of Cranio-Maxillofacial Surgery 36(8):477-480 (2008).

Oh et al., "The Causes of Early Implant Bone Loss: Myth or Science?" J Periodontol 73(3):322-333 (2002).

Ottman et al., "Optimized Piezoelectric Energy Harvesting Circuit Using Step-Down Converter in Discontinuous Conduction Mode," IEEE Transactions on Power Electronics 18(2):696-703 (2003).

Papaspyridakos et al., "A systematic review of biologic and technical complications with fixed implant rehabilitations for edentulous patients," Int J Oral Maxillofac Implants 27(1):102-110 (2012).

Pjetursson et al., "A systematic review of the survival and complication rates of fixed partial dentures (FPDs) after an observation period of at least 5 years: I. implant-supported FPDs," Clin Oral Implants Res 15(6):625-642 (2004).

Pontoriero et al., "Experimentally induced peri-implant mucositis. A clinical study in humans," Clin Oral Impl Res 5(4):254-259 (1994).

Ramadass et al., "A Batteryless Thermoelectric Energy Harvesting Interface Circuit With 35 Mv Startup Voltage," IEEE J Solid State Circuits 46(1):486-487 (2010).

Renvert et al., "Non-surgical treatment of peri-implant mucositis and peri-implantitis: A literature review," J Clin Periodontol 35(Suppl. 8):305-315 (2008).

Renvert et al., "Re-osseointegration on previously contaminated surfaces: A systematic review," Clin Oral Implants Res 20:216-227 (2009).

Rosen et al., "Peri-implant Mucositis and Peri-Implantitis: A Current Understanding of their Diagnoses and Clinical Implications," J Periodontol 84(4):436-443 (2013).

(56) References Cited

OTHER PUBLICATIONS

Sailer et al., "Cemented and screw-retained implant reconstructions: A systematic review of the survival and complication rates," Clin Oral Implants Res 23(Suppl. 6):163-201 (2012).

Sakka et al., "Factors associated with early and late failure of dental implants," Journal of Investigative and Clinical Dentistry 3(4):258-261 (2012).

Salvi et al., "Reversibility of experimental peri-implant mucositis compared with experimental gingivitis in humans," Clin Oral Implants Res 23(2):182-90 (2012).

Skalak, "Biomechanical considerations in osseointegrated prostheses," J Prosthet Dent 49(6):843-848 (1983).

Staedler et al., "Harmonic Nanocrystals for Biolabeling: A Survey of Optical Properties and Biocompatibility," ACS Nano 6(3):2542-2549 (2012).

Wada et al., "Enhanced piezoelectric properties of barium titanate single crystals with different engineered-domain sizes," J Appl Phys 98(1):014109 (2005) 8 pgs.

Wang et al., "Health, Maintenance, and Recovery of Soft Tissues around Implants," Clin Implant Dent Relat Res 18(3):618-634 (2016).

Weber et al., "Peri-implant soft-tissue health surrounding cement- and screw-retained implant restorations: A multi-center, 3-year prospective study," Clin Oral Implants Res 17(4):375-379 (2006).

Zhou et al., "An ultrasonically controlled switching system for power management in implantable devices," Biomed Microdevices 20(2):42 (2018) 9 pgs.

Zitzmann et al., "Experimental peri-implant mucositis in man," J Clin Periodontol 28(6):517-523 (2001).

* cited by examiner

Peri-implant
mucositis
(inflammation)
102

Peri-implantitis
(bone loss)
104

LED

SDI

Rectifier
Circuitry

| 3/12/2020 | HV | spot | det | mag ⊞ | HFW | ⊢———— 30 µm ————⊣ |
| 5:33:28 PM | 10.00 kV | 3.0 | ETD | 2499x | 82.9 µm | |

| 3/12/2020 | HV | spot | det | mag ☐ | HFW | ⊢————— 30 μm —————⊣ |
| 5:08:38 PM | 10.00 kV | 3.0 | ETD | 5000x | 82.9 μm | |

Trenches for
dental resin
(1-3 composite)

Dental crown
by BTNPs
(0-3 composite)

Folded & stacked
microfabricated PCBs

SMART DENTAL IMPLANT SYSTEM FOR AMBULATORY DENTAL CARE

CROSS-REFERENCE TO RELATED APPLICATIONS

This application is a continuation of International Application No. PCT/US2021/037223, filed on Jun. 14, 2021, which claims priority to U.S. Provisional Patent Application No. 63/038,494, filed on Jun. 12, 2020, the entire contents of each of which are incorporated by reference herein.

BACKGROUND

Certain techniques for osseointegrated dental implants can replace missing teeth, while preserving and stimulating the natural bone, but exhibit limited bioactivity (e.g., therapeutic or prophylactic agent release for a limited time) in the context of preventing peri-implant diseases. Peri-implant diseases are inflammatory conditions that affect the soft and hard tissues surrounding a dental implant. Under healthy conditions, peri-implant soft tissues protect the osseointegrated implant against bacterial invasion by enveloping implant-supported restorations. The soft tissue adjacent to these restorations, however, can be less effective than that of natural teeth in resisting bacterial invasion due to the lack of true connective tissue attachment and reduced vascular supply resulting in enhanced vulnerability to peri-implant diseases.

Peri-implant diseases can be classified into two categories: peri-implant mucositis and peri-implantitis. Peri-implant mucositis can be caused by the accumulation of dental plaque (i.e., bacterial biofilms) at the soft tissue-implant interface. The ensuing local inflammatory response of peri-implant mucositis can lead to peri-implantitis. Peri-implantitis can result in both soft tissue inflammation and alveolar bone loss. This alveolar bone loss can, in turn, cause dental implant failure. Dental implant failure can result in discomfort, painful, and costly surgical replacement of failed implants, as well as a potential breakdown of overall oral health.

Good plaque control on the part of patients and routine mechanical instrumentation by a dental professional can be the most effective means of preventing peri-implant diseases but can be insufficient due to poor patient compliance. Furthermore, existing techniques such as the use of systemic antibiotics for treating peri-implant disease are unpredictable and exhibit low success rates (i.e., less than 60%).

Accordingly, there exists a need for a technique for an advanced dental implant system with enhanced biological activity to prevent peri-implant diseases.

SUMMARY

Smart dental implant systems and methods for ambulatory dental care are disclosed herein.

In some embodiments, the disclosed subject matter includes a crown, adapted to mimic a patient's anatomy and location of the smart dental implant system. The crown can include piezoelectric nanoparticles, disposed on a surface of the crown and adapted to generate electricity from a patient's oral motion. In some embodiments, the disclosed subject matter includes an abutment coupled to the crown. The abutment can include an energy harvesting circuit, operationally coupled to the piezoelectric nanoparticles and adapted to harvest the electricity, and a micro LED array, operationally coupled to the energy harvesting circuit and adapted to photobiomodulate surrounding peri-implant soft tissue. In some embodiments, the disclosed subject matter further includes a metal post, adapted for insertion into a patient's jawbone, and a retaining screw, adapted to couple the metal post to the abutment.

In some embodiments of the disclosed subject matter, the patient's oral motion can include at least one of chewing, biting, and brushing. In some embodiments, the energy harvesting circuit can include an AC-to-DC rectifier, adapted to convert the electricity into a DC voltage, and a power management unit, adapted to store the DC voltage. In some embodiments, the abutment can include an LED driver circuit, adapted to generate two different voltage levels and frequencies such that the micro LED array can be adapted to photobiomodulate surrounding peri-implant soft tissue at multiple wavelengths. In some embodiments, the micro LED array can include at least four micro LED disposed, disposed 90 degrees apart, such that the micro LED array can be adapted to photobiomodulate surrounding peri-implant soft tissue. In some embodiments, the crown can have sufficient mechanical strength to withstand large biting forces. In some embodiments, the dental crown can have a two-phase composite configuration for enhanced mechanical strength.

In some embodiments, the disclosed subject matter includes inserting a metal post into a patient's jawbone, coupling a dental implant to the metal post, wherein piezoelectric nanoparticles are disposed on a surface of the dental implant such that the piezoelectric nanoparticles generate electricity from a patient's oral motion, harvesting the electricity from the piezoelectric nanoparticles as an energy source, and photobiomodulating surrounding peri-implant soft tissue with the harvested electricity and paired electronics.

In some embodiments of the disclosed subject matter, the piezoelectric nanoparticles can be fused in a dental material to create the crown. In some embodiments, the piezoelectric nanoparticles can be barium titanate nanoparticles. For example, the barium titanate nanoparticles can be fused in the dental material at a concentration of between 0% and 40% by weight. In some embodiments, the barium titanate nanoparticles can be infused in the dental material with a ceramic dental material by a sintering process. In non-limiting embodiments, the barium titanate nanoparticles can be infused in the dental material as a bulk material by a sintering process.

In some embodiments, the piezoelectric nanoparticles can have further adapted to have an anti-biofilm effect.

In some embodiment of the disclosed subject matter, the dental implant can be coupled to the metal post with a retaining screw. In some embodiments, the harvesting can include converting the electricity into a DC voltage and storing the DC voltage as the harvested electricity. In some embodiments, the patient's oral motion can include at least one of chewing, biting, and brushing. In some embodiments, the photobiomodulating can include multiple wavelengths.

The accompanying drawings, which are incorporated and constitute part of this disclosure, illustrate the disclosed subject matter.

Figure 1:
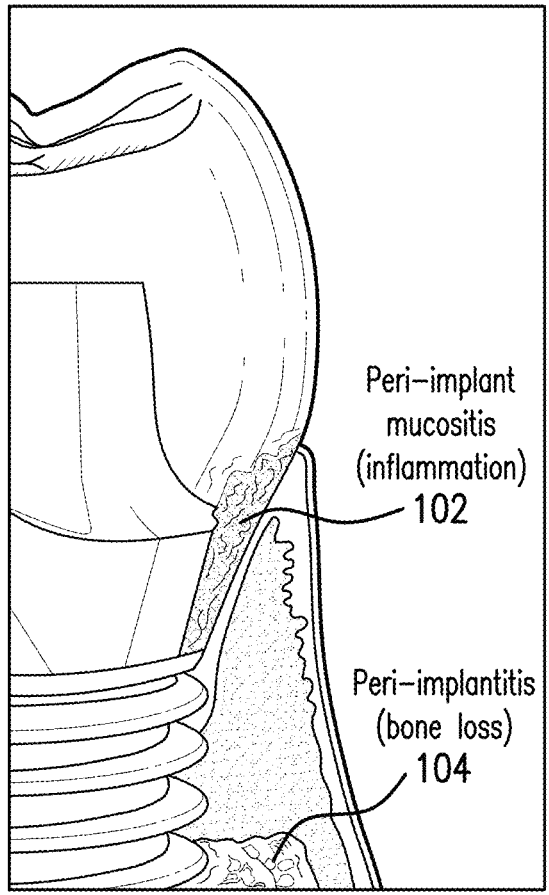
FIG. 1 is a diagram illustrating an existing implant with peri-implant mucositis and peri-implantitis.

Throughout the drawings, the same reference numerals and characters, unless otherwise stated, are used to denote like features, elements, components or portions of the illustrated embodiments. Moreover, while the present invention will now be described in detail with reference to the Figs., it is done so in connection with the illustrative embodiments.

DETAILED DESCRIPTION

Techniques for a smart dental implant system for ambulatory dental care are presented. The smart dental implant system can include a crown and an abutment. The crown can mimic a patient's anatomy and location of the smart dental implant system, and the abutment can be coupled to the crown. Piezoelectric nanoparticles can be placed on a surface of the crown and adapted to transform a patient's oral motion into electricity. The abutment can include an energy harvesting circuit, which harvests the electricity from the piezoelectric nanoparticles, and a micro LED array, which photobiomodulates surrounding peri-implant soft tissue using the harvested electricity. The smart dental implant system can also include a metal post, which can be inserted into a patient's jawbone, and a retaining screw, which can couple the abutment to the metal post.

FIG. 1 is a diagram illustrating an existing implant with peri-implant mucositis and peri-implantitis. Peri-implant diseases can be classified into two categories: peri-implant mucositis 102 and peri-implantitis 104. Peri-implant mucositis 102 can be caused by the accumulation of dental plaque (i.e., bacterial biofilms) at the soft tissue-implant interface. The ensuing local inflammatory response of peri-implant mucositis 102 can lead to peri-implantitis 104. Peri-implantitis 104 can result in both soft tissue inflammation and alveolar bone loss. This alveolar bone loss can, in turn, cause dental implant failure.

Figure 2A:
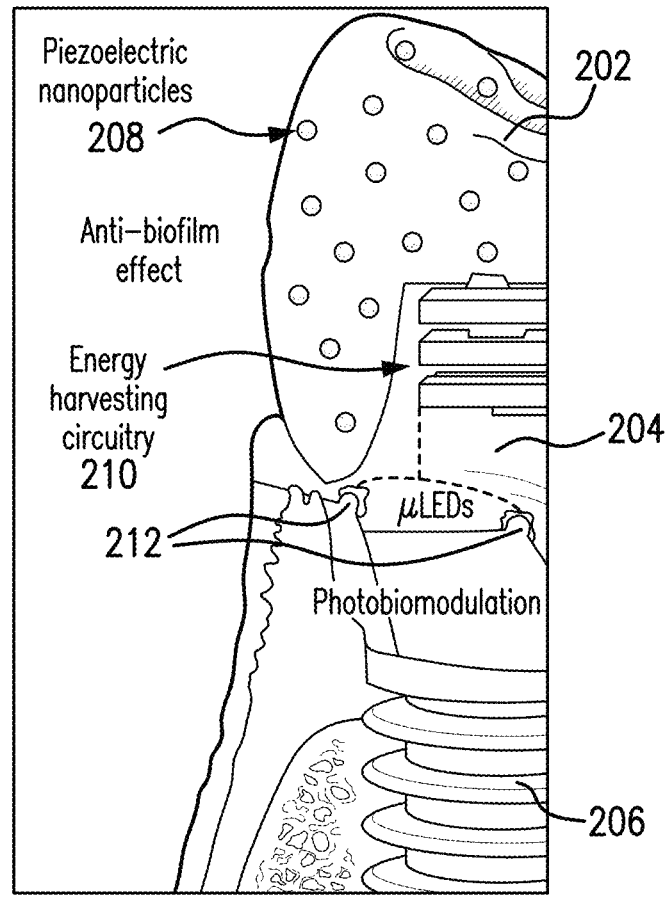
FIGS. 2A-2C are diagrams of a smart dental implant system in accordance with some embodiments of the disclosed subject matter.
Figure 2B:
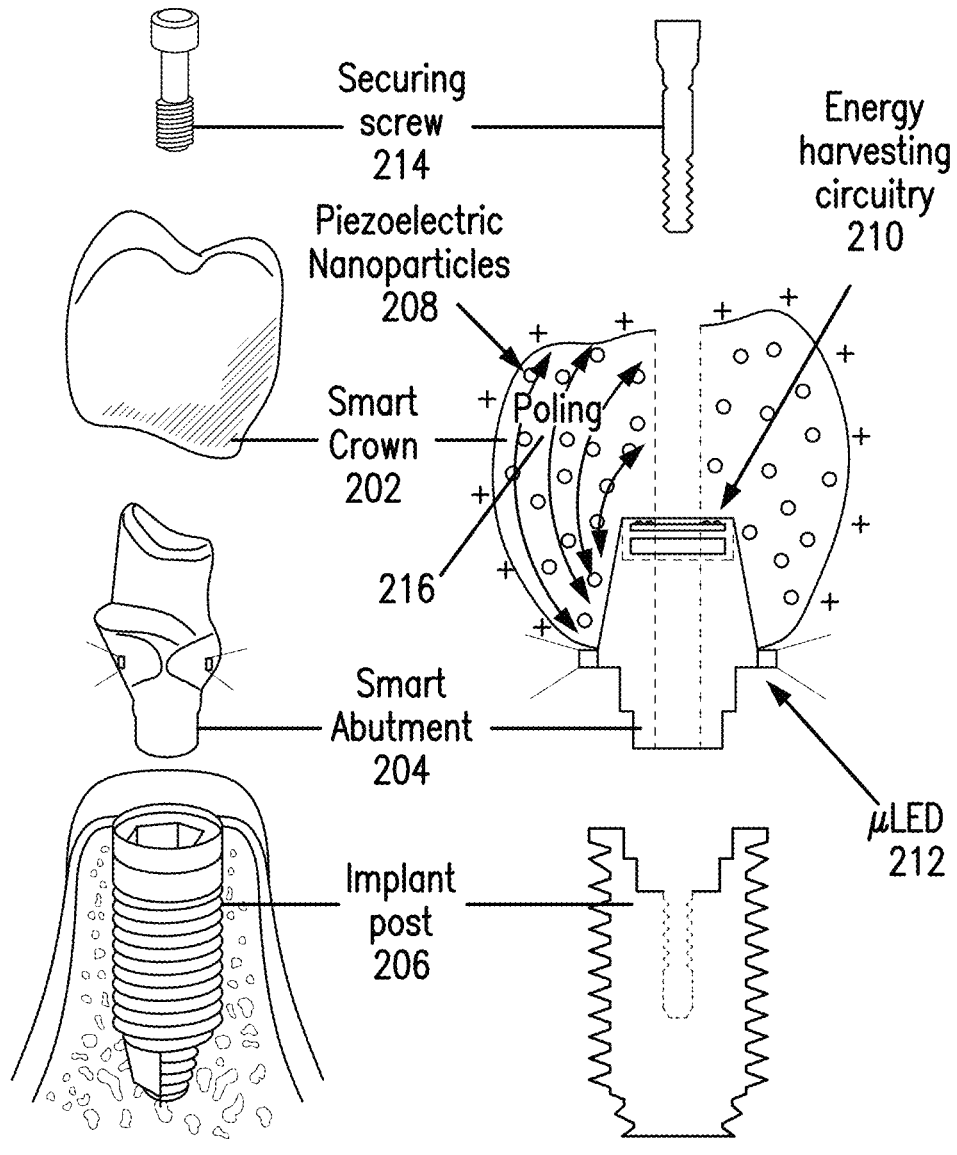
Figure 2C:
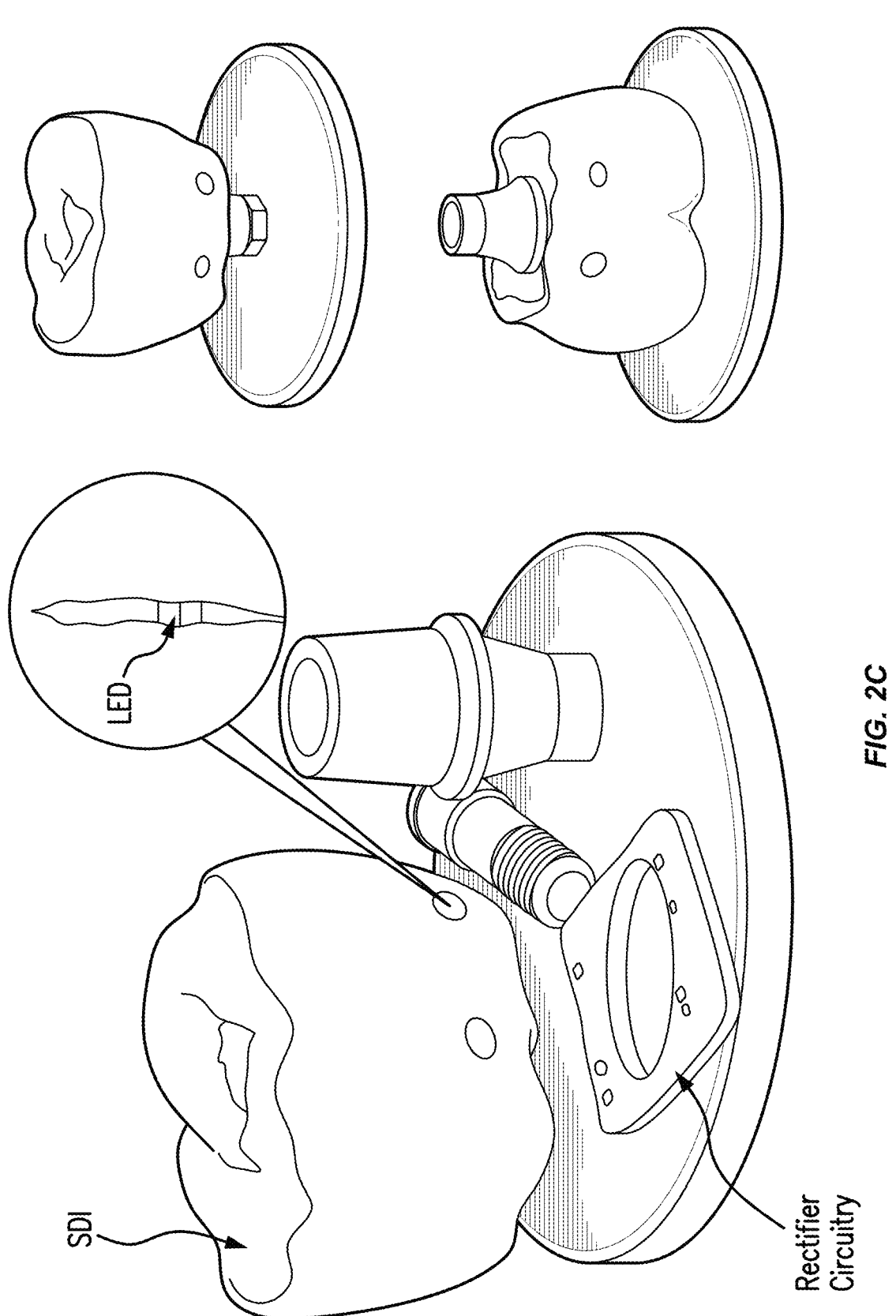

FIGS. 2A-2C are diagrams of a smart dental implant system in accordance with some embodiments of the disclosed subject matter. The smart dental implant (SDI) system can be used for ambulatory dental care and can include a crown 202 and an abutment 204. The crown 202 can transform human oral motion (e.g., chewing, biting, brushing, etc.) into electrical power by fusing piezoelectric nanoparticles 208 into a dental material. For example, the dental material can include two-part dental material or a ceramic-type dental material. The piezoelectric nanoparticles 208 can be fused into the two-part dental material, such as a resin, by mixing the piezoelectric nanoparticle and the dental material. Alternatively, the piezoelectric nanoparticles 208 can be fused into the ceramic-type dental material, such as ceramic (e.g., Zirconia) or porcelain, prior to the sintering, which can result in a single dental crown. To enable the production of a patient-specific dental crown that mimics the patient's unique anatomy, 3D printing technology can create the crown. The piezoelectric nanoparticles can be infused in a 3D printable dental crown (C&B Micro Filled Hybrid, NextDent) and 3D printed in an open mode (Form 3, Formlab Inc.).

As shown in FIG. 2B, a poling process 216 can be done by applying a high voltage (>2 kV/mm) while heating over Curie temperature. The poling process 216 can improve or optimize the electrical performance of the piezoelectric nanoparticles 208 by aligning randomly oriented electrical polarization to achieve the enhanced piezoelectric performance by order of magnitudes. The piezoelectric nanoparticles 208 can also have an anti-biofilm effect by preventing adhesion or selectively killing only adhered bacteria, thereby reducing or minimizing antibacterial resistance and disturbing microbiome homeostasis.

The electrical energy generated by piezoelectric nanoparticles 208 can be properly managed for optimal LEDs irradiance. The abutment 204 can include an energy harvesting circuit 210, and a micro LED array 212. The energy harvesting circuit 210 can be operationally coupled to the piezoelectric nanoparticles 208, such that the energy harvesting circuit 210 can harvest the electricity generated by the piezoelectric nanoparticles 208. The micro LED array 212 can be operationally coupled to the energy harvesting circuit such that the micro LED array 212 receives the harvested electricity from the energy harvesting circuit 210. The micro LED array can then enable in situ photobiomodulation ("PBM") therapy of surrounding peri-implant soft tissue.

The crown 202 and the abutment 204 can be assembled together using a dental adhesive (Panavia, Kuraray Medical Inc.). A retaining screw 214 can securely mount the crown-abutment assembly onto the metal implant post 206. The metal post 206 can be inserted into a patient's jawbone, and the retaining screw 214 can then couple the metal post to the abutment.

Figure 3A:
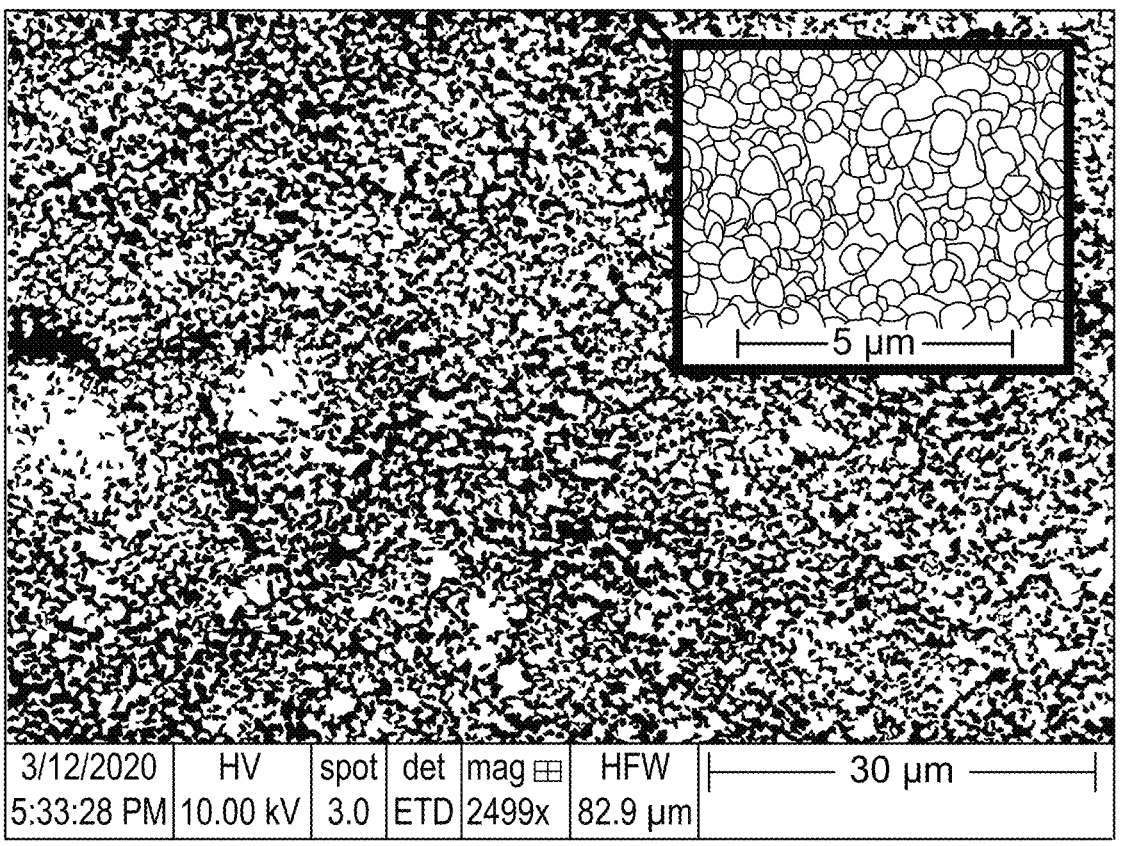
FIGS. 3A-3C illustrate SEM imaging and Raman characterization of piezoelectric nanoparticles in accordance with some embodiments of the disclosed subject matter.
Figure 3B:
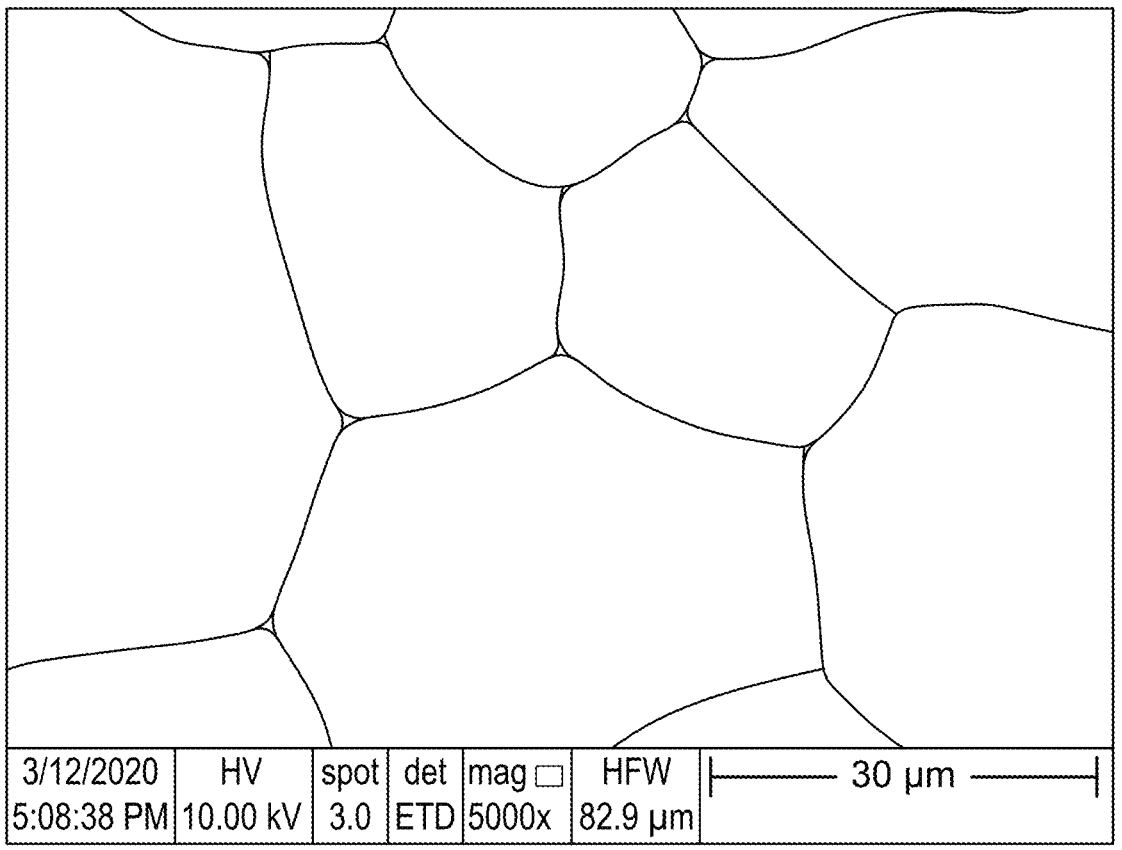
Figure 3C:
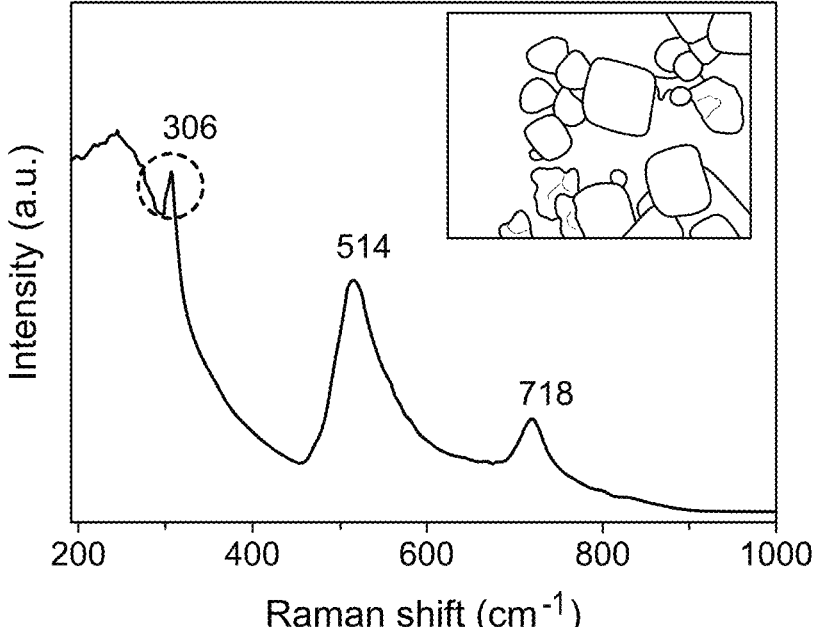

FIGS. 3A-3C illustrate SEM imagings and Raman characterization of piezoelectric nanoparticles in accordance with some embodiments of the disclosed subject matter. The piezoelectric nanoparticles can be infused on the surface of the crown. For example, the piezoelectric nanoparticles can be barium titanate ($BaTiO_3$) nanoparticles ("BTO-NPs") (400 nm, US Research Nanomaterials Inc.) as depicted in FIG. 3A. The BTO-NPs are suitable due to their piezoelectricity and low cytotoxicity. The BTO-NPs can be infused in a 3D printable crown (C&B Micro Filled Hybrid, NextDent) using open mode 3D printing (Form 3, Formlab Inc.). The BTO-NPs can also be sintered with dental material and create a single bulk material, as depicted in FIG. 3B. As shown in FIG. 3C, the peak at 306 cm$^{-1}$ can indicate the signature of the tetragonal (i.e., piezoelectricity). Additionally, an optical property of the BTO-NPs (i.e., their white color) can be suitable for dental material since it can provide a balance between opacity and translucency of the crown to blend in with existing teeth. Other inorganic and organic piezoelectric nanoparticles with low cytotoxicity can also be suitable. For example, suitable inorganic piezoelectric nanoparticles can include barium titanate-based, sodium potassium niobite-based, and bismuth titanate-based ceramics, as well as zinc oxide-based nanostructures. Suitable organic piezoelectric nanoparticles can include polyvinylidene difluoride.

Prior to the fabrication, a two-part dental material (e.g., resin) can be stirred overnight on a rotational mixer platform. After BTO-NPs are introduced, it was stirred for another 24 hours. The two-part dental material can be then degassed for about 30 minutes. The molar design can be obtained from a 3D scanned design. The molar design can be modified and included a honeycomb design to enforce the mechanical strength. After 3D printing, the hollow region of the honeycomb structure can be filled with BTO-NPs-infused dental material, followed by UV curing. The fabricated molar can be then post-processed, which involved cleaning by IPA then ethanol under heated sonication. After 2 hours of sonication, the Smart Crown can be cleaned again using ethanol.

Alternatively, the piezoelectric nanoparticles can be introduced into a ceramic-type dental material, such as Zirconia.

Figures 4A, 4B, 4C, 4D, 4E, 4F, 4G, 4H:
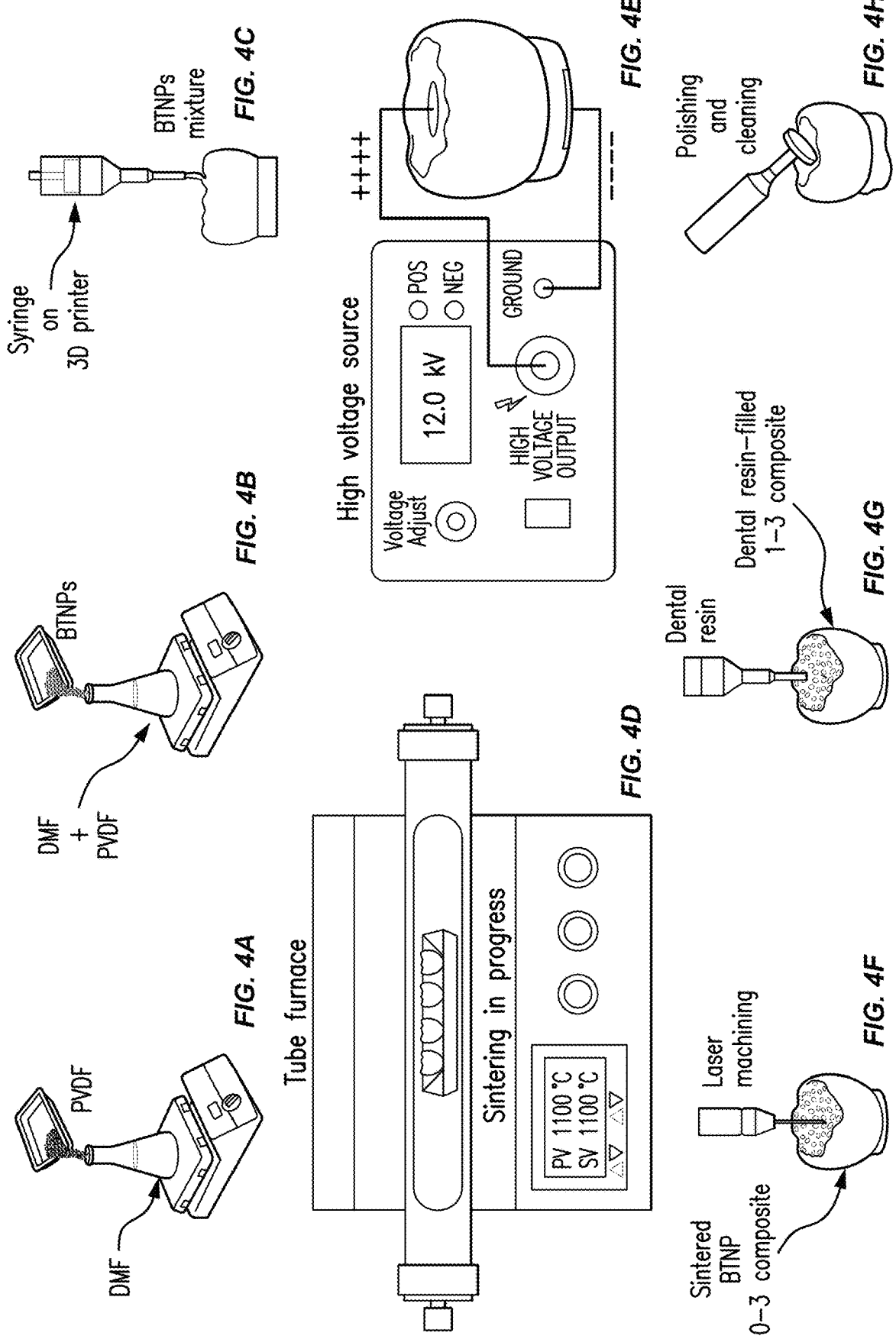
FIGS. 4A-4H are diagrams of an exemplary fabrication procedure in accordance with some embodiments of the disclosed subject matter.
Figure 4I:
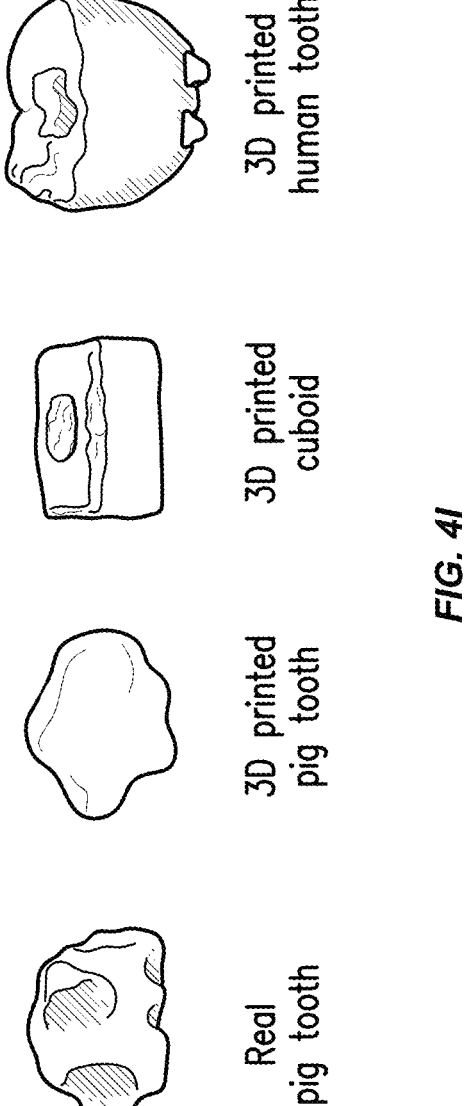
FIG. 4I is a photo of real pig tooth, 3D printed pig tooth, 3D printed cuboid, and 3D printed human tooth in accordance with some embodiments of the disclosed subject matter.

The combination of the piezoelectric nanoparticles and the ceramic-type dental material can be sintered. The BTNPs colloid suspension can be prepared, as illustrated in FIGS. 4A-4H. The base binder solution can be first prepared by mixing zirconia or polyvinyl fluoride (PVDF) in N,N-dimethylformamide (DMF; Sigma Aldrich) by a weight ratio of 1:8.8 at 80° C. for 15 min, as seen in FIG. 4A. The BTO-NPs are slowly added into the binder solution while continuously stirring by hand until it reached a high-volume concentration, as seen in FIG. 4B. The empirical result found that the binder solution could take up to 332 wt. % of BTO-NPs. The BTO-NPs suspensions are then loaded to a syringe, followed by installing to a paste extrusion 3D printer, as seen in FIG. 4C. In some embodiments, the printing speed can be adjusted to about 1 mm/s with a z-resolution of about 400 μm. The printed SDI can be then dried at 120° C. for 2 hours to evaporate DMF, completing the green material. The post-processing of debinding and sintering can be subsequently performed using a tubing furnace (FIG. 4D). The 3D printing allows creating a variety of dental specimens without compromising antibiofilm and mechanical properties. FIG. 4I shows an example of 3D printing, such as a human dental molar, animal teeth, or simple cuboid, implying that the SDI can be prepared to accommodate any anatomic structure.

Figure 4J:
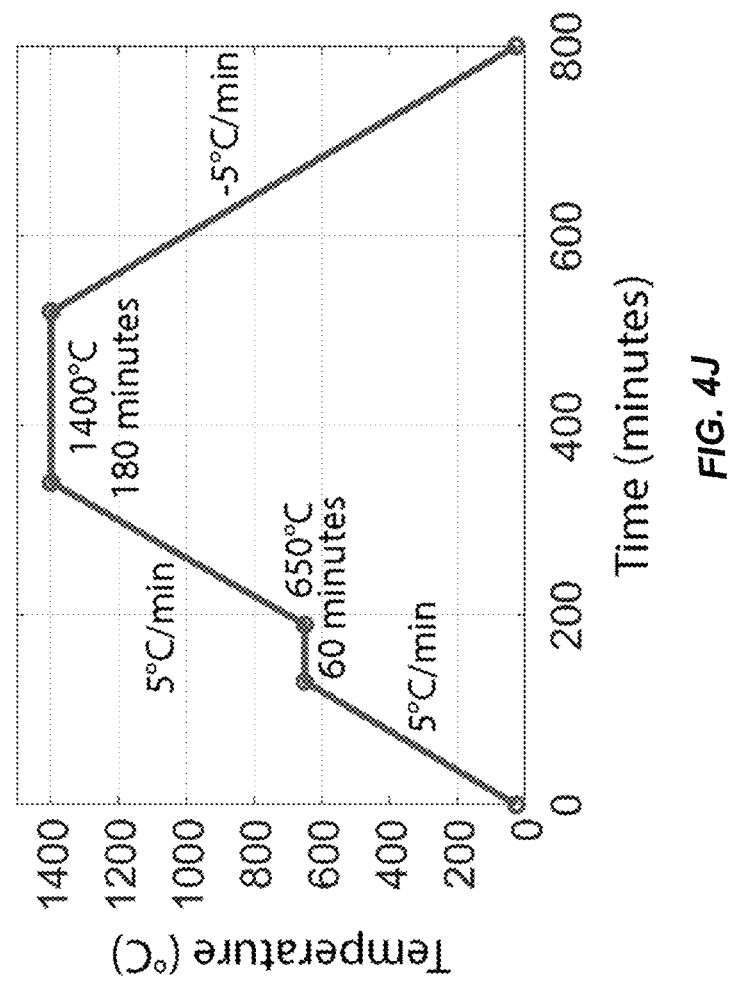
FIG. 4J is a graph showing an exemplary sintering temperature profile in accordance with some embodiments of the disclosed subject matter.
Figure 4K:
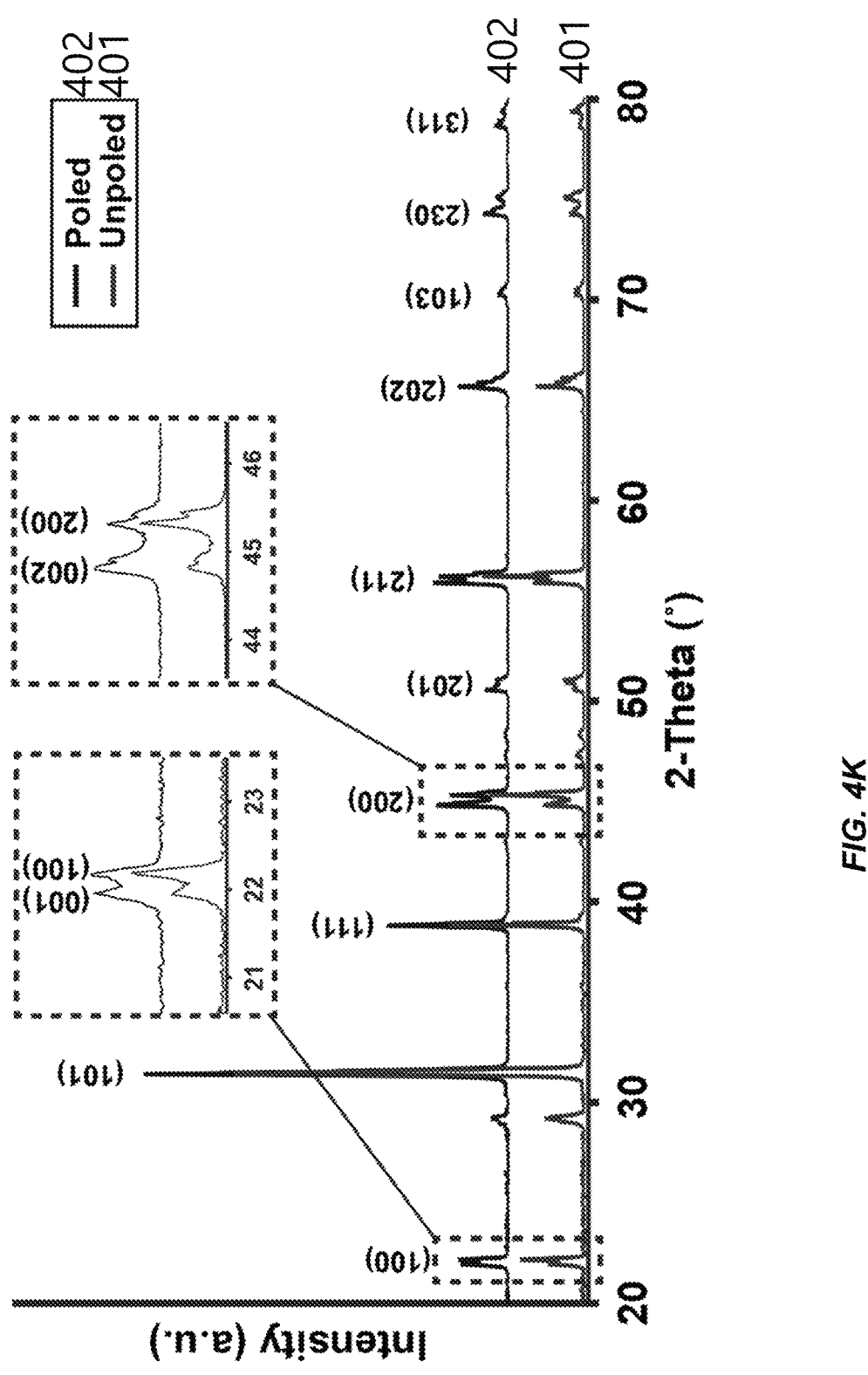
FIG. 4K is a graph showing X-ray diffraction patterns of the fabricated $BaTiO_3$ ceramic before and after poling in accordance with some embodiments of the disclosed subject matter.

FIG. 4J shows an exemplary temperature profile: about 650° C. for about 1 hour (ramp rate=5° C./min) for debinding, followed by sintering at about 1400° C. for about 3 hours (ramp rate=5° C./min). After the post-process, the SDI can be poled to align randomly oriented ferroelectric domains. For that, the SDI can have temporary electrodes at the top and bottom by applying silver epoxy. The SDI can then be placed on a custom-made poling stage that can have a copper bottom plate and a spring-loaded needle electrode from the top. The poling stage can be equipped with a built-in heating element in a silicone oil bath. FIG. 4E illustrates the polling process. Using the poling stage and a high voltage source, a uniform electric field of 1 kV/mm can be applied across the SDI while the temperature of the silicone oil bath can be set below the Curie temperature for BTO-NPs (80° C.). In some embodiments, the total poling time can be 4 hours. FIG. 4K illustrates the X-ray diffraction patterns of the fabricated $BaTiO_3$ ceramic before and after poling. The tetragonal phase of $BaTiO_3$ ceramic can be confirmed by the peak splitting at $2\theta$ near 45°. In non-limiting embodiments, the peak ratio of (002) and (200) planes can be enhanced from about 0.43 under the un-poled sample 401 to about 1.23 under the poled sample 402. It can indicate that crystal domains can be reoriented through the poling. In some embodiments, the (001) diffraction peak of the poled sample at about 22° can be significant compared to that of the un-poled sample, indicating a large number of crystal domains are aligned along the same direction.

Figure 4L:
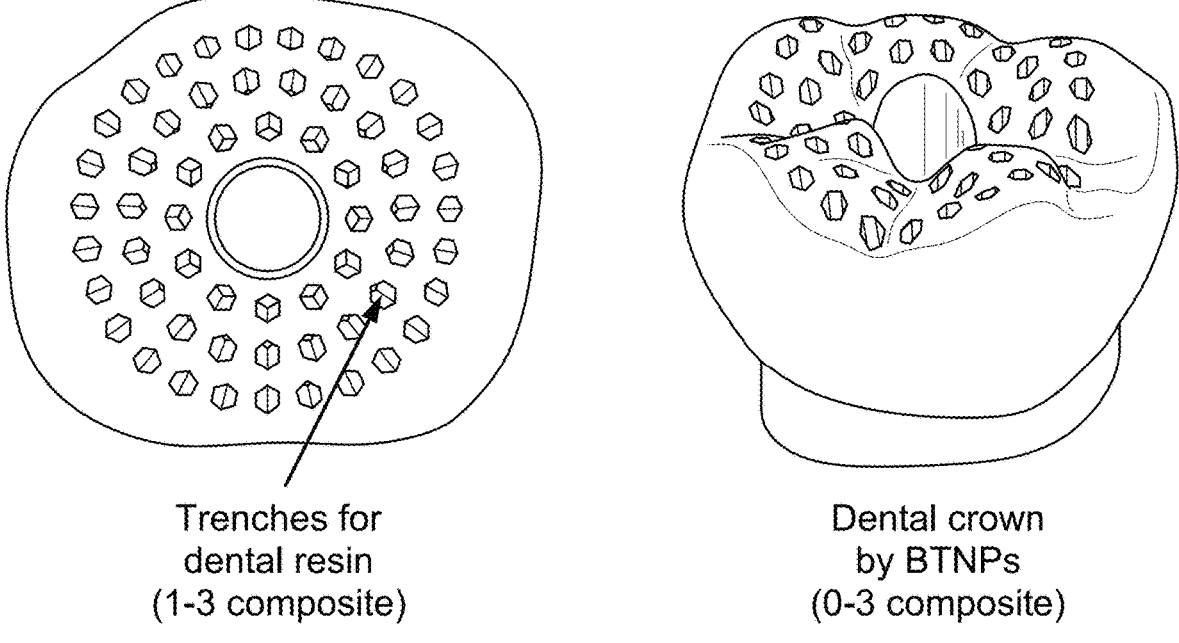
FIG. 4L is an exemplary diagram of the smart dental implant (SDI) crowns that include a two-phase composite in accordance with some embodiments of the disclosed subject matter.

In certain embodiments, for the sintered sample, the SDI crown can be composed of a two-phase composite, as shown in FIG. 4L: the dispersion of piezoelectric nanoparticles (0-3 composite; i.e., 0-dimension BTNPs embedded in 3-dimensions matrix) and traditional dental material attributes (1-3 composite; i.e., 1-dimension dental resin pillar embedded in 3-dimensions BTNPs-based composite). The two-phase composite can allow multiple functions. For example, the 0-1 composite can offer the piezoelectric nanoparticles to afflict more directly with oral biomechanics for efficient energy harvesting, and the 1-3 composite by the traditional dental material provides adequate mechanical strength under the mechanical stresses due to these oral motions.

The mixed mode composite can be fabricated by modifying the SDI crown. For example, the SDI crown can be laser machined to create honeycomb-inspired trenches for 1-3 composite configuration (as seen in FIG. 4F), which reinforces the mechanical strength. FIG. 4L shows a laser machined base of the 1-3 composite. The trench size can be 0.5 to 1 mm in diameter. The trenches are filled with ultraviolet (UV) light curable dental crown resin (C&B Micro Filled Hybrid, NextDent), as seen in FIG. 4G. In some embodiments, various dental materials (e.g., dental resin, metal, and/or ceramic (e.g., zirconia) can be used for filling. Prior to filling the trenches, the dental resin needs to be stirred overnight on a rotational mixer platform. The sidewall of the dental crown can also be enforced by coating with the dental resin. After filling, the SDI can be degassed for an hour, followed by UV light curing. The fabricated piezoelectric dental crown can be sanded and polished for the final touch. As the filling process can create residues on the surface, the dental crown can be further polished and adjusted to the desired shape as necessary. In some embodiments, the dental crown can be a two-phase composite for enhanced mechanical strength. For example, the dispersion of piezoelectric nanoparticles (0-3 composite; i.e., 0-dimension barium titanate nanoparticle embedded in 3-dimensions matrix) and traditional dental material attributes (1-3 composite; i.e., 1-dimension dental resin pillar embedded in 3-dimensions barium titanate nanoparticle-based composite).

To test the conformality of the BTO-NPs in dental material, the 3D printed crown can be stored in 55° C. phosphorus buffered solution (PBS, Sigma) for 24 hours to monitor if the BTO-NPs escape from the dental material. Four different concentrations (5, 10, 20, and 30 wt %) can be examined in the dental material for their leaching behavior. BTO-NPs of 30 wt % can be dispersed homogeneously and alleviated agglomeration in the dental material.

Figure 5A:
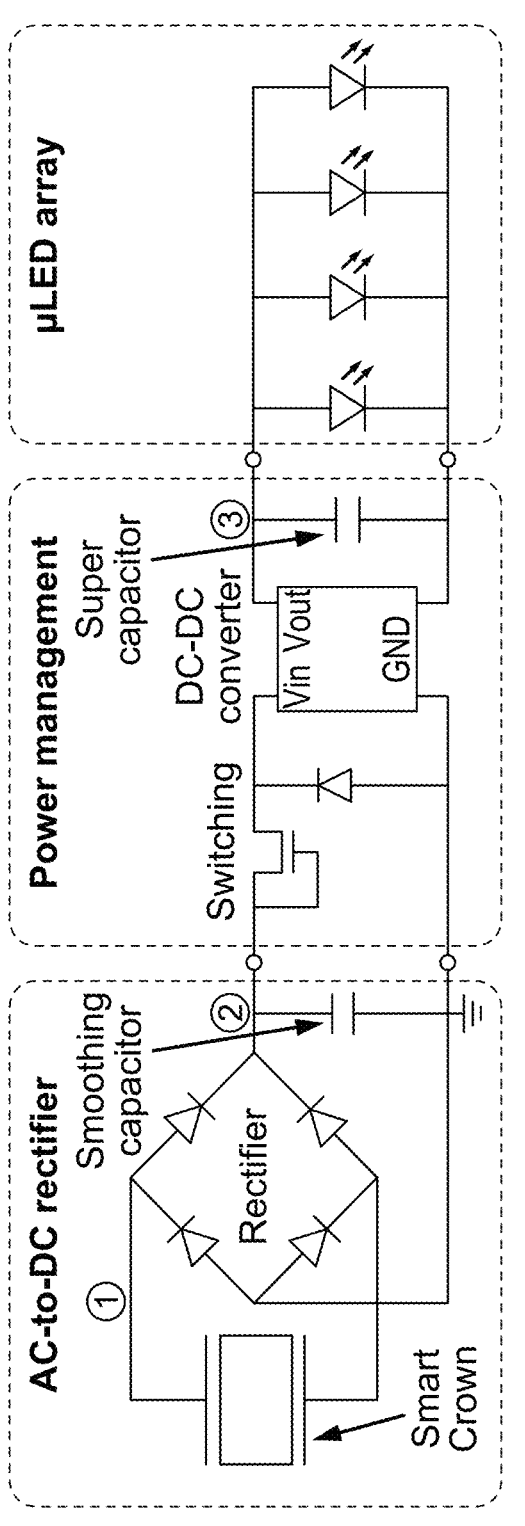
FIGS. 5A-5E are diagrams of the circuitry in the abutment in accordance with some embodiments of the disclosed subject matter.
Figure 5B:
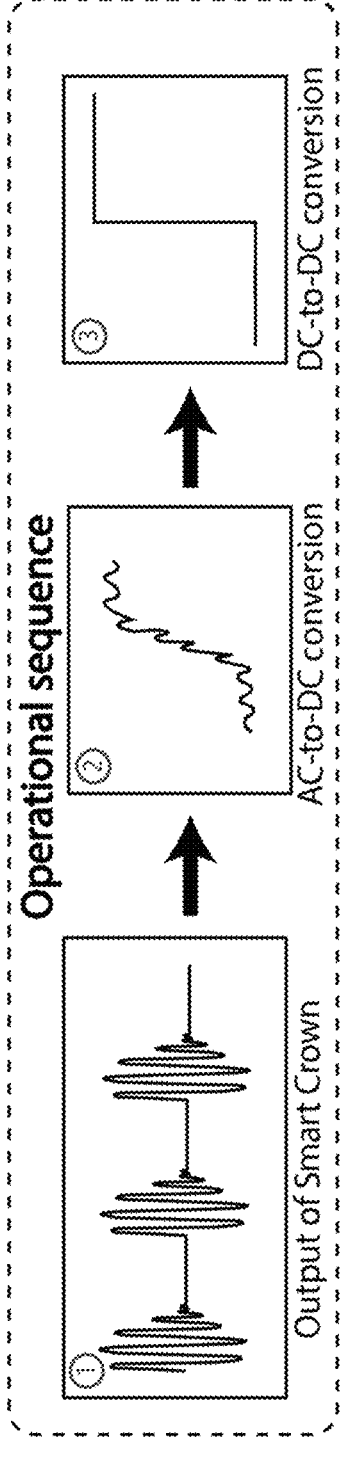
Figure 5C:
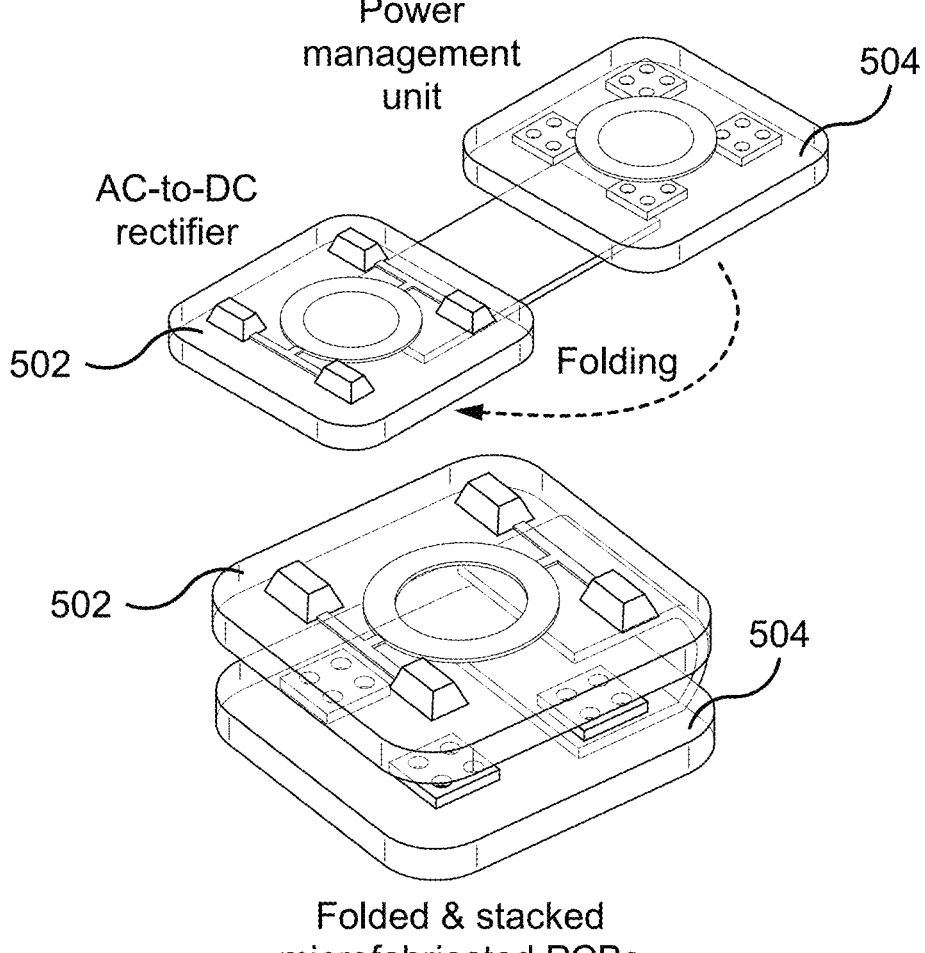

FIGS. 5A-5E are diagrams of the circuitry in the abutment in accordance with some embodiments of the disclosed subject matter. The energy harvesting circuit can be optimized for low-frequency applications, such as human oral motion. As depicted in FIGS. 5A and 5C, the energy harvesting circuit 210 can include an AC-to-DC rectifier 502 and a power management unit 504. The AC-to-DC rectifier 502 can be coupled to the piezoelectric nanoparticles 208 in the crown 202 and, as shown in FIG. 5B, can convert human oral motion into electrical power. The power management unit 504 can store up to 3.3 V from a rapid charge (1 min.), which will sufficiently operate for 90 minutes (an effective time duration based on a 30-minute meal, 3 times a day). Such power generation can operate the micro LEDs array 212. For example, low-current micro LEDs can require only 1.8 V for full brightness.

As depicted in FIG. 5C, the energy harvesting circuitry can be fabricated via microfabrication for further miniaturization. The circuit can be divided into multiple blocks and fabricated on a flexible substrate (e.g., copper-clad polyimide, Pylex, Dupont Inc.). A ribbon cable can connect each block so that it can be folded and stacked. Sub-mm sized discrete electronic components can include micro LEDs (SML-P11x, Rohm; $1\times0.6\times0.2$ mm$^3$), transistors (FK4B01110L1, Panasonic; $0.6\times0.6\times0.1$ mm$^3$), a supercapacitor (CHP3225A, Seiko; $3\times2\times1$ mm$^3$, Schottky diodes (CMRSH-4DO, Central Corp; $0.9\times0.7\times0.4$ mm$^3$), and resistors (CRCW0201, Vishay; $0.6\times0.3\times0.2$ mm$^3$). Upon the assembly of all discrete components, the abutment can be coated with Parylene-C (5 μm) for protection.

Figure 5D:
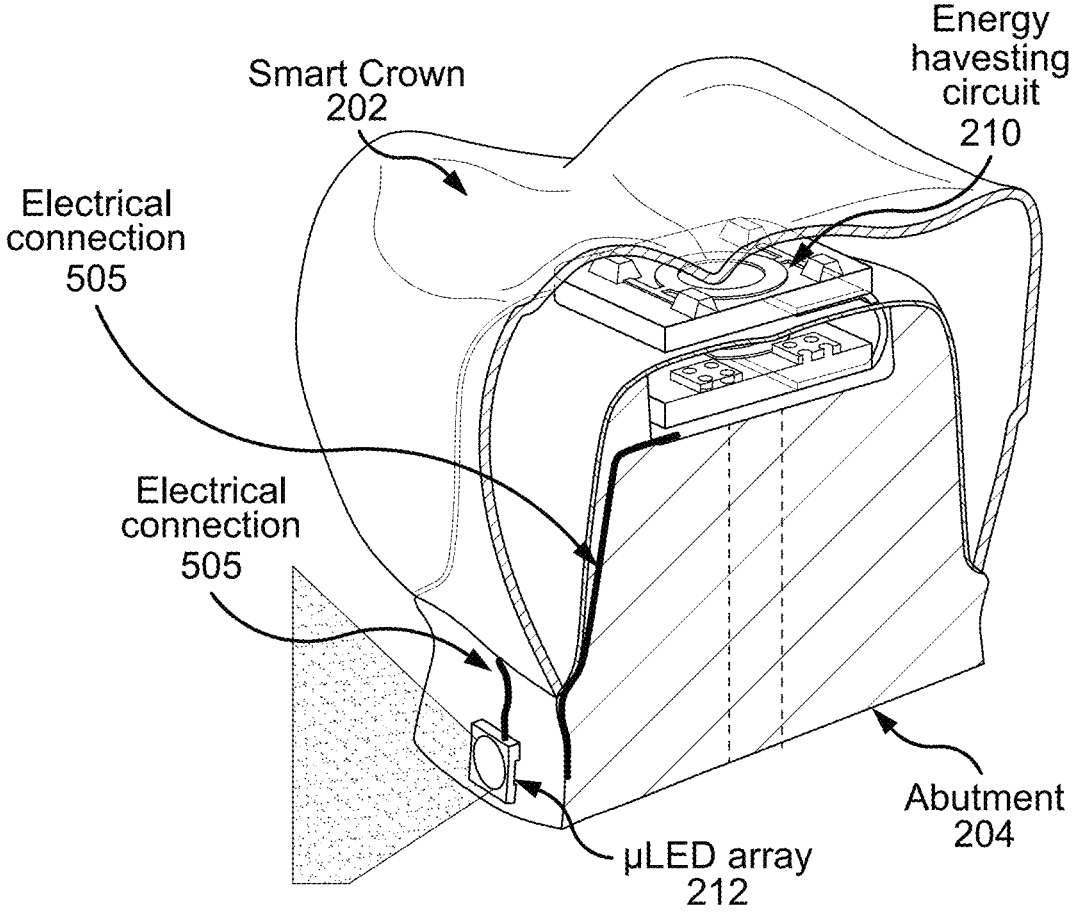

As depicted in FIG. 5D, the energy harvesting circuitry 210 and micro LEDs 212 can be integrated on an abutment 204. The abutment 204 can have a small space at the top to house the miniaturized circuit and to interface with the crown 202 and grooves at the bottom, where peri-implant diseases are commonly found, to place and connect micro LEDs 212 via electrical connection 506. At least four micro LEDs, one every 90 degrees, can be used to cover all surrounding peri-implant soft tissue.

Figure 5E:
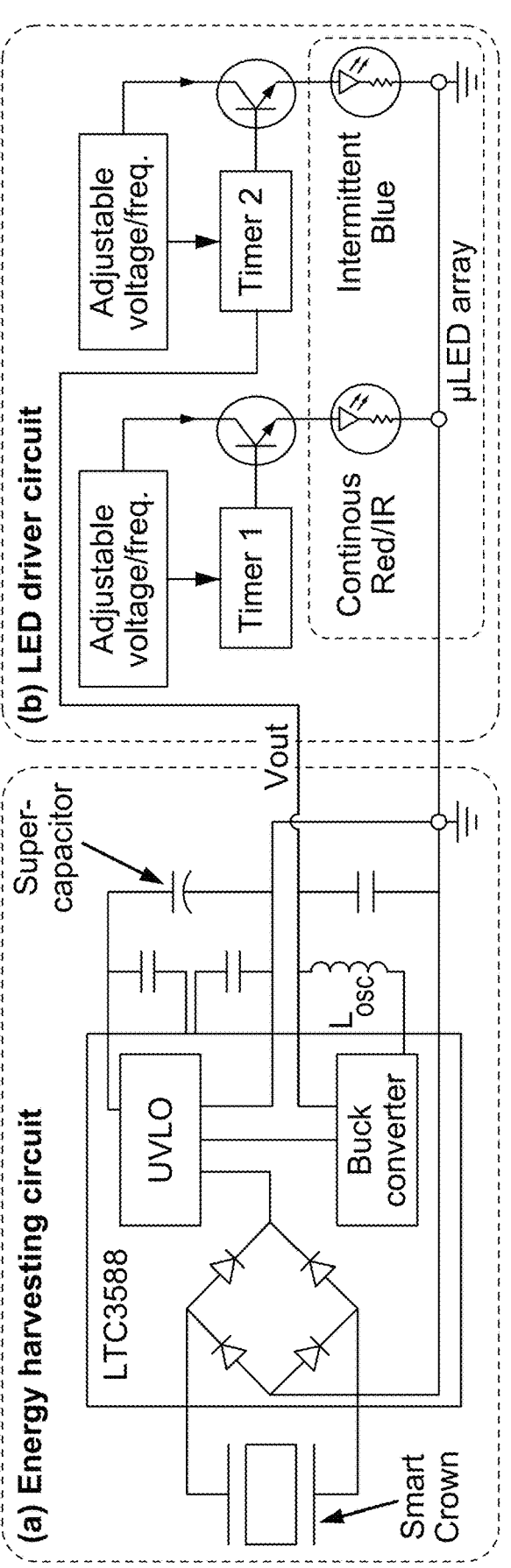

As shown in FIG. 5E, in some embodiments, the energy harvesting circuit can convert the human oral motion into a DC voltage using an internal low-loss rectifier in an energy harvesting IC chip (LTC3588, Linear Technology). The IC chip can manage the DC voltage using an under-voltage lockout (UVLO) that allows charge to accumulate in a supercapacitor (CPH3225A, Seiko) until the bulk converter can efficiently transfer the stored charge to the output. Note that unlike a battery, the supercapacitor voltage drops linearly as it supplies energy. Thus, it can be important to maintain an ultralow quiescent current of the energy harvesting ICs ($I_Q$=450 nA) to allow a substantial drop in voltage and yet draw the required current.

In some embodiment, the abutment can include an LED driver circuit. The LED driver circuit can generate two different voltage levels and frequencies for multi-wavelength PBM (MW-PBM). The LED driver circuit can include two individually tuned timer (via resistor-capacitor circuits) with switching circuits (via a transistor) to simultaneously operates multiple of low power LEDs ($I_F$~2 mA). The voltage levels can adjust from 0.2 to 2.8V, and frequencies could be adjusted to 0, 5, or 500 Hz with a 50% duty cycle (CW, $PW_5$, or $PW_{500}$).

Figure 6A:
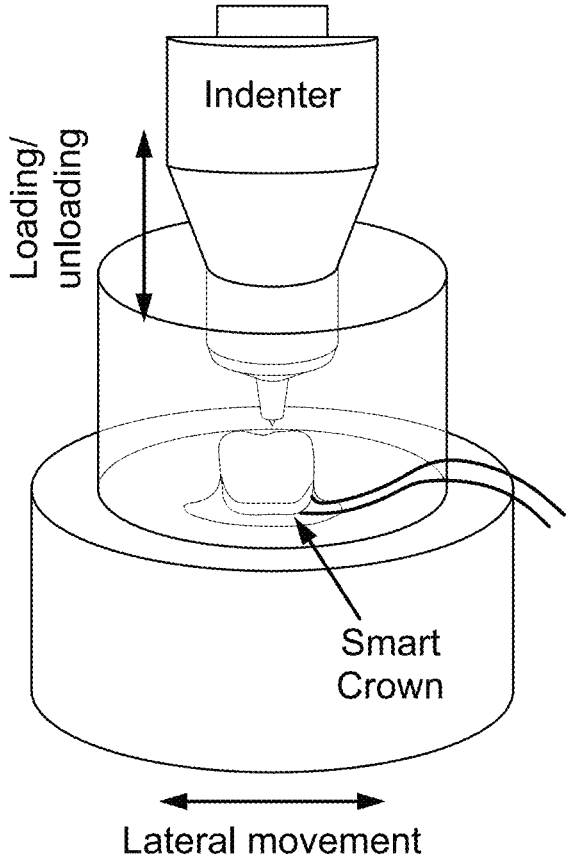
FIG. 6A is a diagram of an exemplary model mimicking a chewing motion.
Figure 7A:
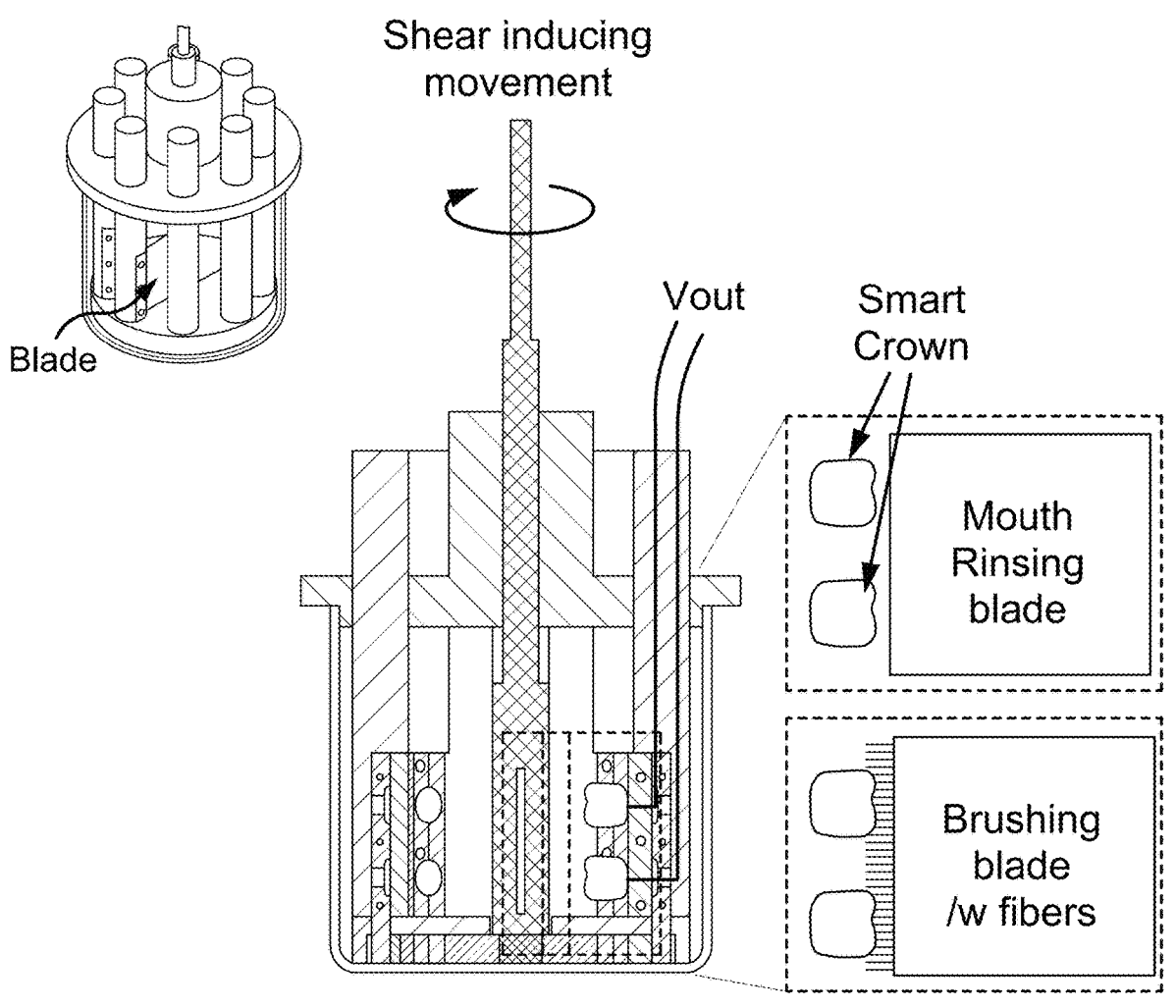
FIG. 7A is a diagram showing an exemplary brushing model in accordance with some embodiments of the disclosed subject matter.

FIGS. 6A and 7A are diagrams from testing that mimic a chewing motion and measures its corresponding voltage output in accordance with some embodiments of the disclosed subject matter. The generation of sufficient electrical power by human oral motion to irradiate LEDs can be needed for efficacious PBM therapy. BTO-NPs can be promising due to their biocompatibility, piezoelectric properties, and non-linear optical features. Thus, whether such piezoelectric dental material can convert chewing motion (as a model human oral motion) into electrical power for LED irradiance can be examined.

Figures 6B, 6C, 6D, 6E:
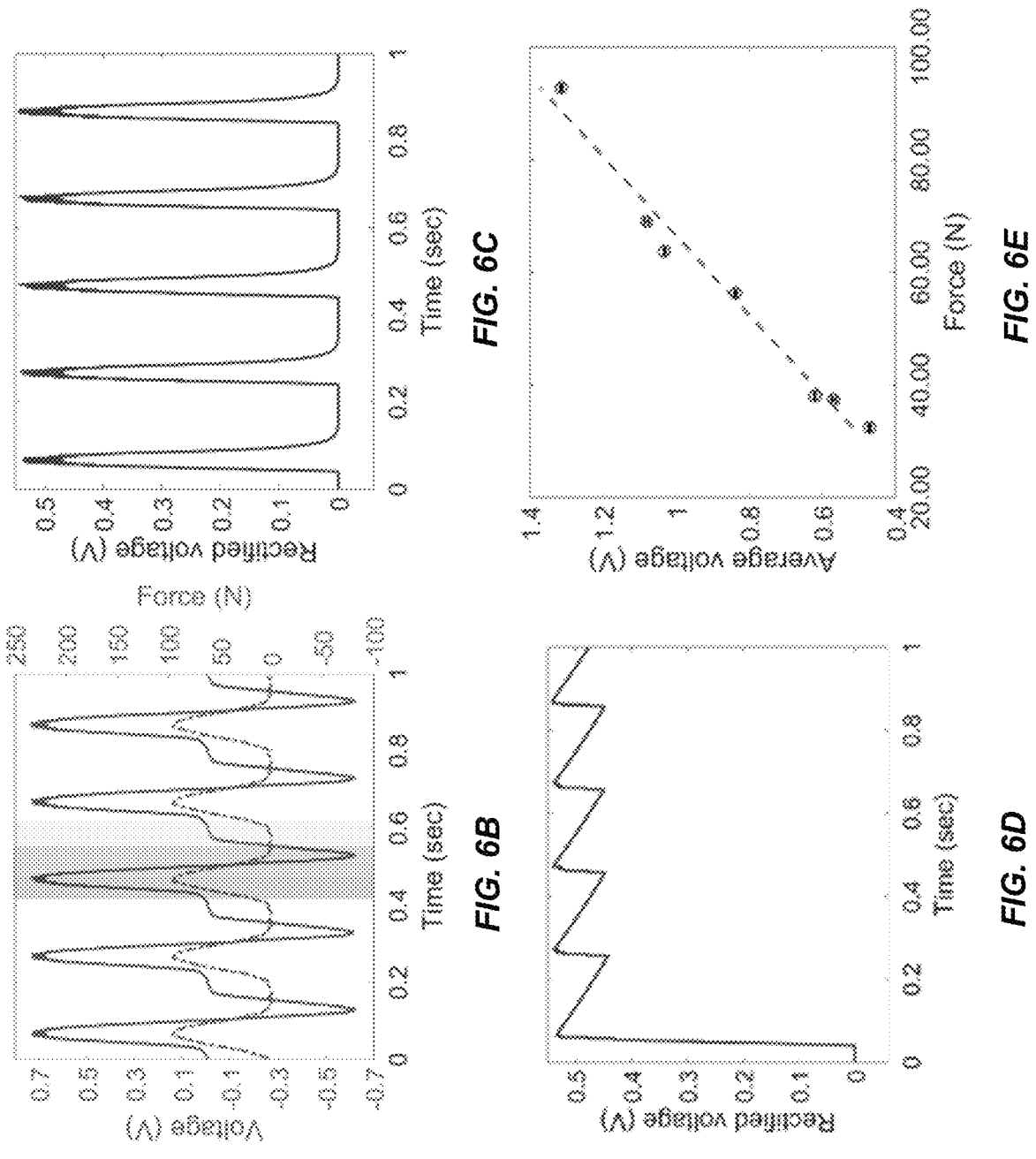
FIG. 6B is a graph showing a representative example of the electrical voltage outputs of the chewing model from an SDI under chewing motion.
FIG. 6C is a graph showing an exemplary electrical voltage output of the chewing model, which is converted into pulse wave (PW) outputs.
FIG. 6D is a graph showing an exemplary rectified output voltage of the chewing model.
FIG. 6E is a graph showing a comprehensive result of average voltage outputs of the SDI under soft food chewing motions.
Figures 7B, 7C, 7D, 7E:
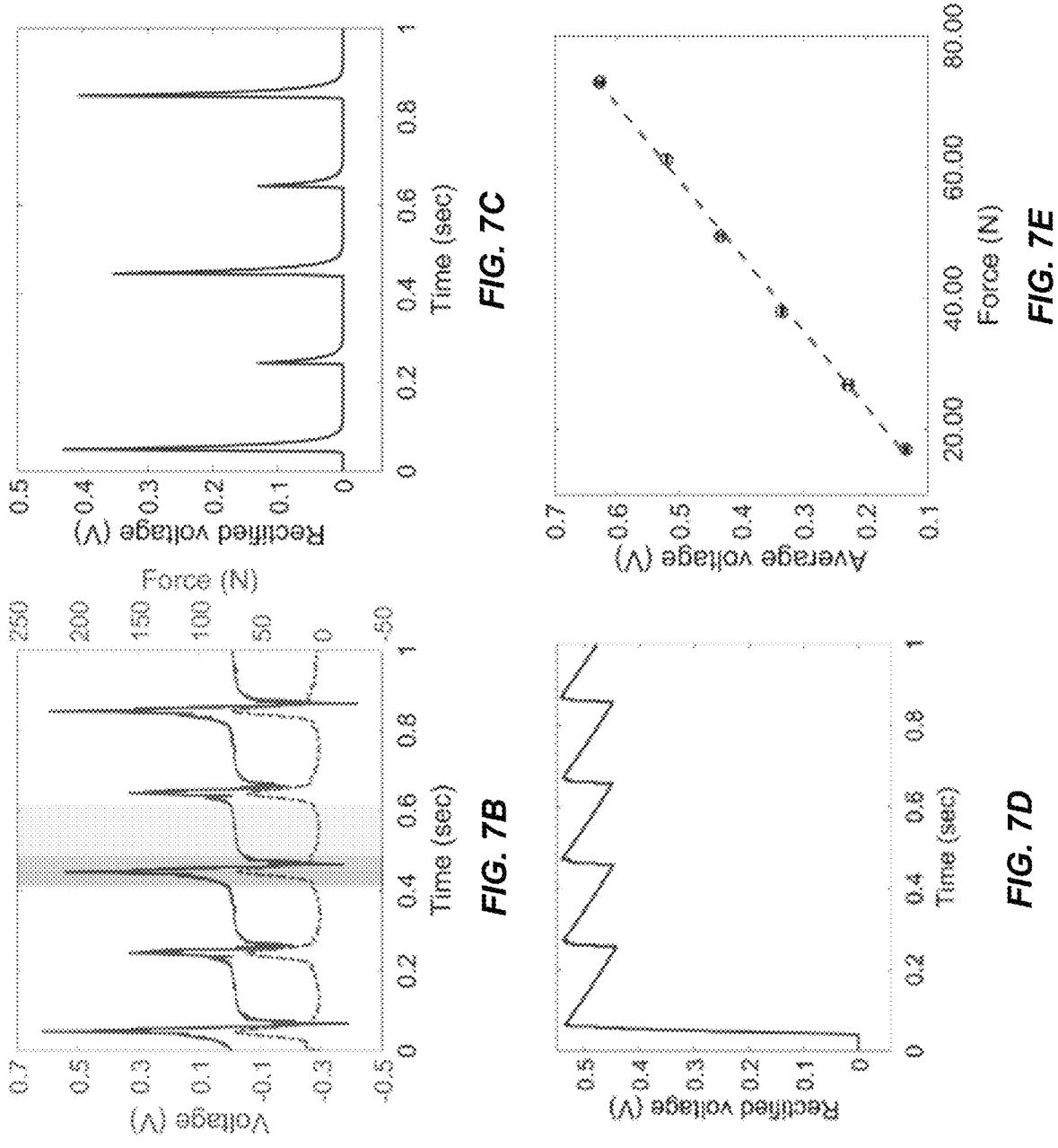
FIG. 7B is a graph showing a representative example of the electrical voltage outputs of the brushing model from an SDI under brushing motion.
FIG. 7C is a graph showing an exemplary electrical voltage output of the brushing model, which is converted into pulse wave (PW) outputs.
FIG. 7D is a graph showing an exemplary rectified output voltage of the brushing model.
FIG. 7E is a graph showing a comprehensive result of average voltage outputs of the SDI under brushing motions.

In certain embodiments, the energy harvesting performance of the SDI can be evaluated using dynamic human oral motion models of chewing and tooth-brushing. The electrical voltages can be measured when the SDIcan be stimulated by chewing motion using a force application machine, which can be capable of simulating antagonist strikes in accordance with controlled parameters, as shown in FIG. 6A. In non-limiting embodiments, to examine the efficiency of mechanical to electrical conversion, the SDI without a circuit can be tested first. FIG. 6B shows a representative example of the electrical voltage outputs from an SDI under chewing motion (e.g., the applied force can be approximately 90 N at a frequency of 5 Hz). The output can show three different regimes: a positive voltage during compression, a negative voltage during decompression, and be followed by an idling trend between two different directions of forces. As an indenter is initiated to compress the SDI, the electrical energy can begin to increase proportionally to the applied force. At the onset of maximum compression (i.e., maximum load), the subsequent decompression can surge in the polarity of voltage generation as the direction of the applied force can be reversed, which can explain the negative voltages. In some embodiments, as an indenter returns to the base position and can be lifted from the SDI, the voltage output can also return to the idle point until the next cycles start. In some embodiments, the empirical piezoelectricity can be measured to be about 202 (±10.87) pC/N. In some embodiments, the electrical voltage output can be managed via a pair of a diode and a capacitor, which converted the sinusoidal voltage outputs into pulse wave (PW) outputs, as seen in FIG. 6C. The PW output deriving LEDs in frequency mode can be beneficial for PBM therapy. While the frequency can be determined by the oral motions, it can be adjusted to continuous wave (CW) by implementing a rectifier circuit with a large capacitor (e.g., 47 μF or above to compensate for the low frequency) as seen in FIG. 6D. FIG. 6E shows a comprehensive result of average voltage outputs of the SDI under soft food chewing motions that ranges from about 30 N to about 100 N (f=5 Hz). The average voltage outputs can be measured to be 0.4 V (±2.6 mV) to 1.3 V (±2.8 mV) as a function of applied chewing force (V=0.014 F+0.058; R2=0.97; where V is voltage and F is applied force FIG. 7A shows a brushing motion that can be applied to the SDI using a custom-made shear force application machine. Similar voltage outputs to the one from the chewing machine can be observed (see FIGS. 7B-7D). Without a circuit, the voltage output induced by a brushing motion can have three regimes, a positive voltage as brush fibers start sweeping in, a negative voltage as brush fibers finish sweeping and slowly lift off from the SDI, and an idle period. In some embodiments, the time duration of rising and declining voltages can be about half of the chewing motion (e.g., 20 msec vs. 40 msec). It can be attributed to the force application direction respect to the poling direction of the SDI. During the fabrication, the SDI can be poled in $d_{33}$ direction (i.e., longitudinal). The chewing motion can be in the same direction as the poling, which can be the preferred direction for energy harvesting in certain situations. In non-limiting embodiments, the brushing motion can be perpendicular to the poling direction, $d_{31}$ (i.e., lateral direction), whose piezoelectric constant relating the open-circuit voltage to the input mechanical stress can be about half of the primary poling direction (measured to be 113 (±4.08) pC/N). Despite half of the piezoelectric constant, the dental crown under brushing motion can generate a comparable voltage output to the chewing motion: 0.7 V (±5.4 mV) vs. 1.0 V (±2.8 mV). The average outputs of the SDIs (n=3) can be linearly proportional to applied forces, as shown in FIG. 7E (V=0.009 F−0.005; R2=0.99). This can be due to the symmetrical nature of geometry (i.e., low aspect ratio) of the SDI that affected a large portion of a dental crown to deform in the longitudinal force even under the lateral brushing motion (the Poisson ratio compensates for the difference in $d_{33}$ and $d_{31}$ constants).

In certain embodiments, the disclosed subject matter provides various human oral motions (e.g., chewing and brushing). FIG. 6A shows the chewing model, which uses a programmable electromechanical universal test machine (311R, TestResources, Inc.). It is capable of simulating antagonist strikes in accordance with controlled parameters by adjusting the traverse paths of the axles and the speeds. A series of complete chewing cycles can be executed onto the distobuccal cusp of SDI. The counterweight can be varied, which can load the antagonists and generates contact pressure during the abrasive motion. In certain embodiments, the soft food chewing motion parameters can be employed (e.g., speed=20-40 mm/s, force=0-200 N, and frequency=1-5 Hz.

FIG. 7A shows the brushing model that uses a custom-design rotational apparatus. The rotation can be induced by a motor (BDC3030, Caframo Limited) that holds a central steel rod with a square blade at the bottom. On the blade, two toothbrush heads can be mounted at each end. The central rod can then be placed on top of a circular platform, which can also hold multiple plastic rods on its edge so that the brush heads can sweep the SDI mounted on a plastic rod as the central rod rotates. In non-limiting embodiments, on the plastic rods, a designated space can be introduced to mount the SDI. The filaments of the brush overlap approximately 5 mm of the SDI. In some embodiments, the brushing motion parameters can be employed (e.g., speed=2 mm/s, normal force=12 N (assuming 600 filaments sweep the SDI on each stroke and normal force due to a single filament can be approximately 20 mN), shear force=15-70 N, and frequency=1-5 Hz).

Figure 8A:
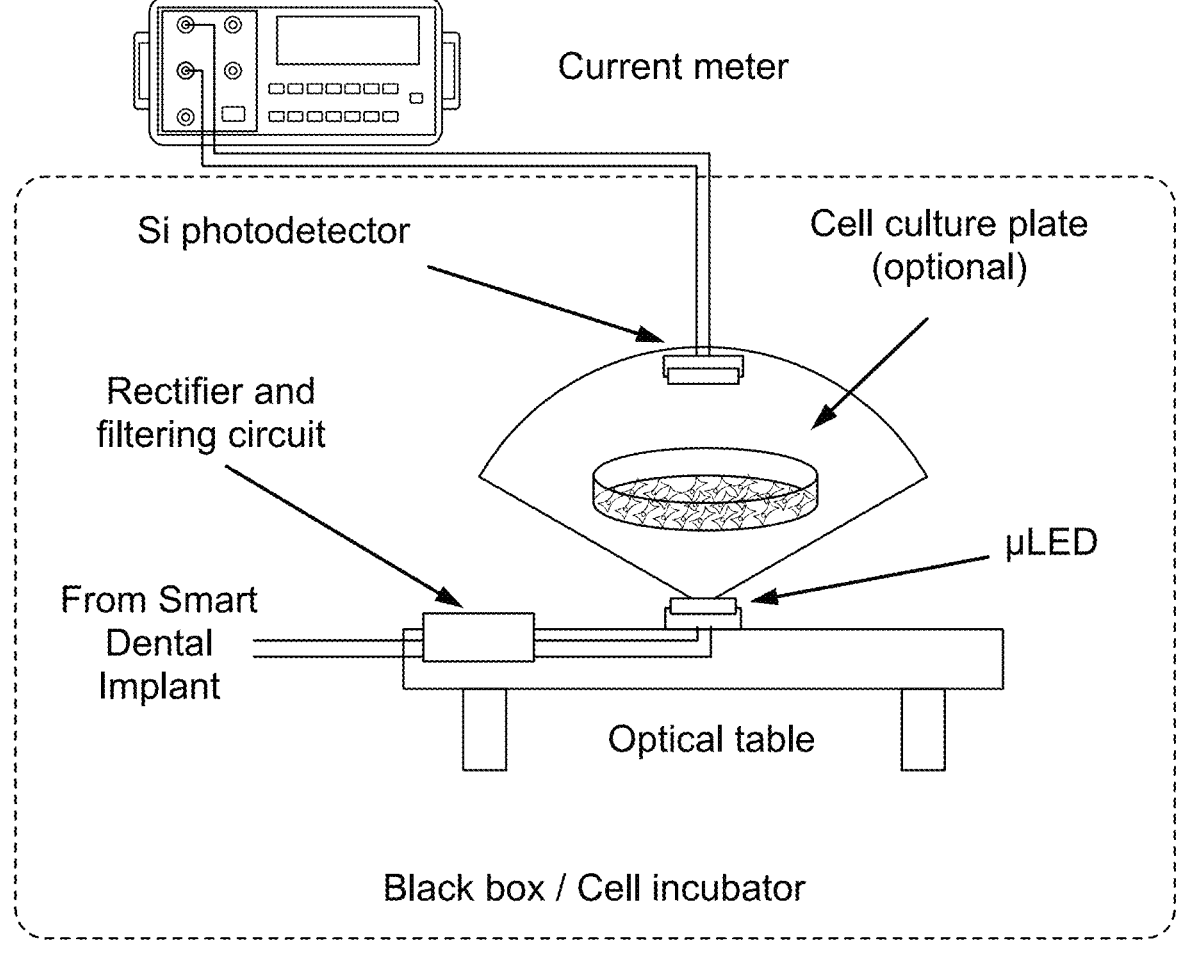
FIG. 8A is a diagram showing an exemplary 8A illustrates a diagram of an exemplary system for light irradiance measurements and in vitro PBM therapy.

FIG. 8A illustrates an exemplary setup for light irradiance measurements as well as in vitro PBM therapy, which can connect the SDI under chewing or brushing machine and electronics, i.e., rectifier and a micro LED. The results of energy harvesting from chewing and brushing motions indicated a low-power LED could be sufficiently powered. The average electrical voltage can be measured to be 1.3 V under chewing motion (e.g., 70 N) or brushing motion (e.g., 100 N). The corresponded light irradiance of the red color LED can be measured to be about 0.3 mW/cm$^2$. For the identical light irradiance, near-infrared LED can be 0.8 V, which can be derived from about 60 N of chewing motion or about 90 N of brushing motion. In certain embodiments, all light measurements can be performed by a silicon photodiode in a black box.

Figure 8B:
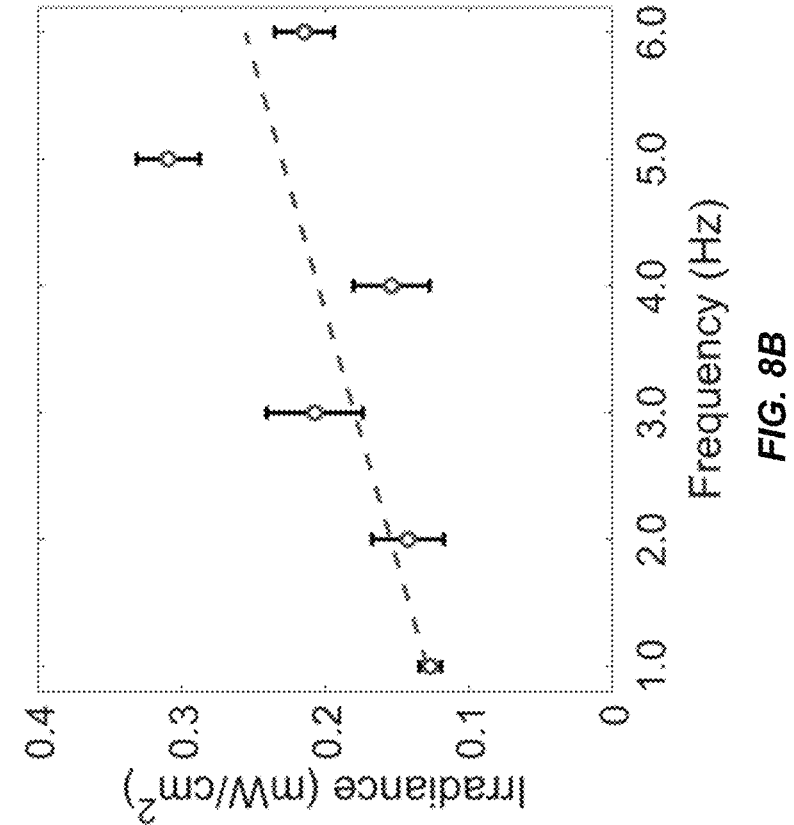
FIG. 8B is a graph showing the average light irradiance from the SDI prototypes according to various PW frequencies.

In some embodiments, the efficacy of photobiomodulation therapy using SDI can be evaluated. For example, a single LED per well can be used to quantify the baseline effects of light intensity to the primary human gingival keratinocytes (HGKs) in near-contact mode. In some embodiments, multiple LEDs can be powered with the SDI under chewing or brushing motion by connecting them in a parallel configuration. In non-limiting embodiments, the SDI-mediated PBM therapy can be evaluated using pulse wave (PW), and continuous wave (CW) as the PW light therapy can be more effective than CW light therapy in certain biological settings. FIG. 8B shows the average light irradiance from the SDI prototypes according to various PW frequencies. The average light irradiance can increase in the higher frequency since a capacitor can be more frequently charged, enhancing the energy harvesting efficiency.

Figure 9A:
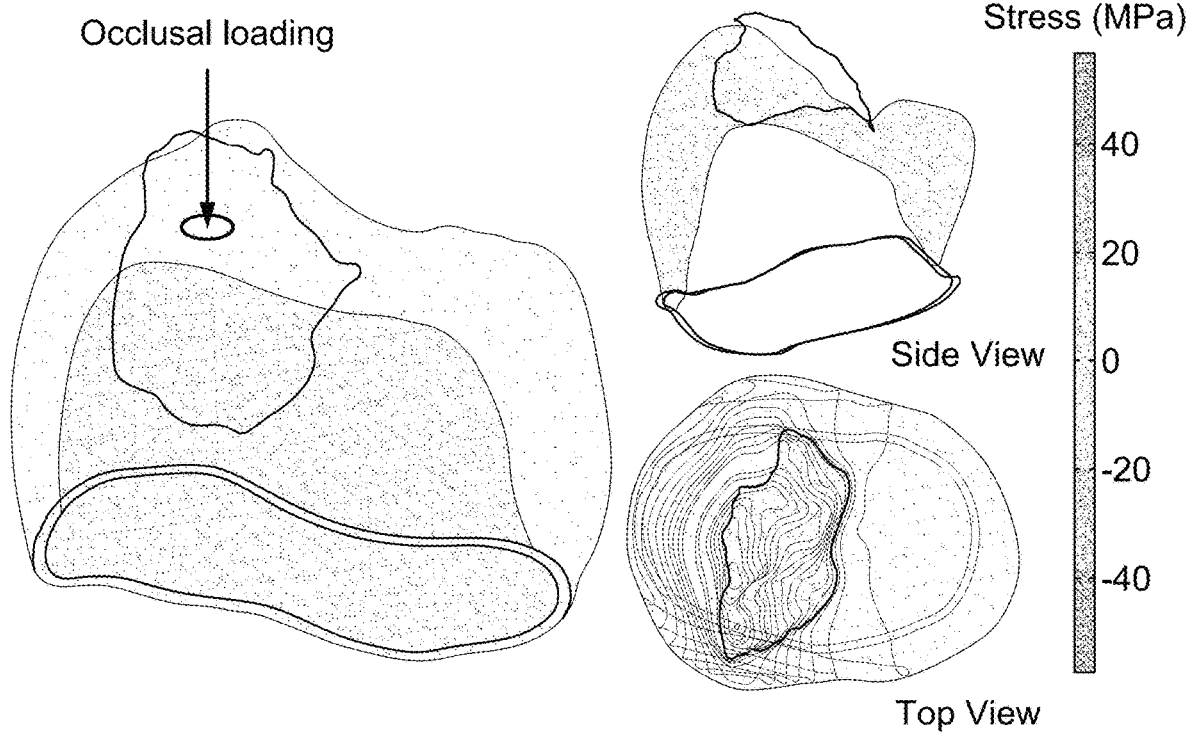
FIG. 9A illustrates a finite element analysis of occlusal loading on the distobuccal cusp in accordance with some embodiments of the disclosed subject matter.

FIG. 9A illustrates a finite element analysis ("FEA") of occlusal loading on the distobuccal cusp in accordance with some embodiments of the disclosed subject matter. The smart dental implant system can have sufficient mechanical strength to withstand large chewing/biting forces as crowns are frequently exposed to those forces particularly in the molar region. For example, the average maximum bite force can be approximately 700-900 N. For dental implants, FEA simulations have been widely used to evaluatemechanical performance, including FDA guidelines. Therefore, an FEA simulation (COMSOL Multiphysics) can be performed to evaluate the stress conditions on the various molar designs. FIG. 6 shows the von-Misses stress simulation results of occlusal loading on the BTO NP-infused dental molar. The simulation results revealed that the engineered dental material can withstand up to 42 MPa von-Misses stress, which can be a clinically acceptable level.

Figure 9B:
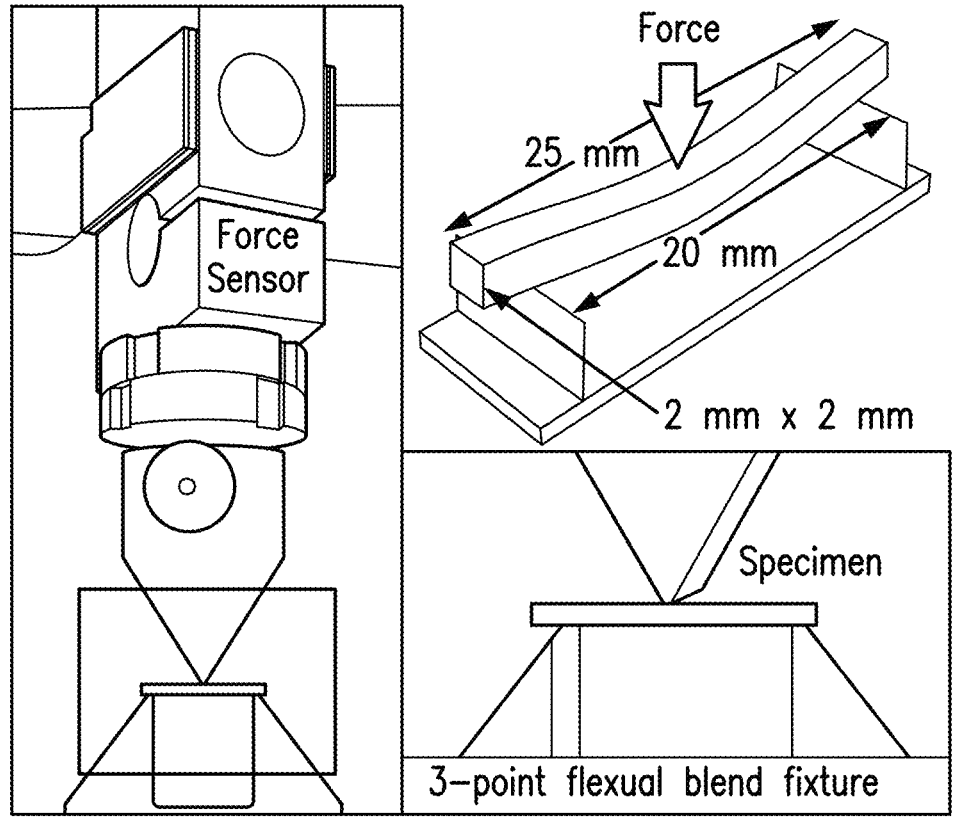
FIG. 9B is a diagram of an exemplary system for a comprehensive mechanical evaluation in accordance with some embodiments of the disclosed subject matter.

An electromechanical universal test machine (310, TestResources Inc.) can be used with ISO 4049 (Dentistry—Polymer-based restorative material)-specific test fixtures and biomedical baths (to simulate body temperature) for the comprehensive mechanical evaluation. As seen in FIG. 9B, 3-points flexural bend fixture can be used. A total ten of 25×2×2 mm³ beam structures are prepared using the engineered dental material. Force and deformation can be substantially measured. The FS and FM can be then calculated using the following:

$$FS = \frac{3FL}{2bh^2} \quad FM = \frac{FL^3}{4dbh^3} \tag{1}$$

where b=beam width (mm), h=beam depth (mm), F=load at a given point on the load-deflection curve (N), L=support span (mm), and d=corresponding deflection at F (mm).

The simulation results can be further validated by measuring the flexural strength ("FS") and factual modulus ("FM") of the smart dental implant crown, containing BTO-NPs in a dental material. Table I summarizes a comparison of the mechanical strength of our SDI to other materials. The dental composite used in the SDI shows FS of 50 MPa and FM of 6630 MPa, which are comparable to the mechanical strengths of dental resins reported elsewhere (FS: 65-130 MPa, FM: 2000-7500 MPa). It indicates that the engineered dental crown can reasonably endure the impact force (flexural strength) while causing lower deflection (flexural modulus).

TABLE I

Mechanical Strength Comparison

| Material | Standard | FS (MPa) | FM (MPa) |
|---|---|---|---|
| BTNPs-infused 0-3 composite/ w 3D printable dental resin 1-3 composite | ISO 4049 | 50 (12.9) | 6630 (1100) |
| 3D printable dental resin (control) | ISO 4049 | 90 (8.0) | 3290 (590) |
| Human dental crown | ISO 4049 | 114-210 | — |
| 3D printable dental resin | ISO 4049 | 65-90 | 1700-2700 |
| Functionalized dental resin with nanodiamond | ISO 4049 | 80-110 | 2000-2800 |
| Enforced dental resin composite with various fillers | ISO 4049 | 83-161 | 3700-16000 |
| Dental resin composite with silica nanostructure | ISO 4049 | 82-120 | 4000-8100 |

Figures 10A, 10B, 10C:
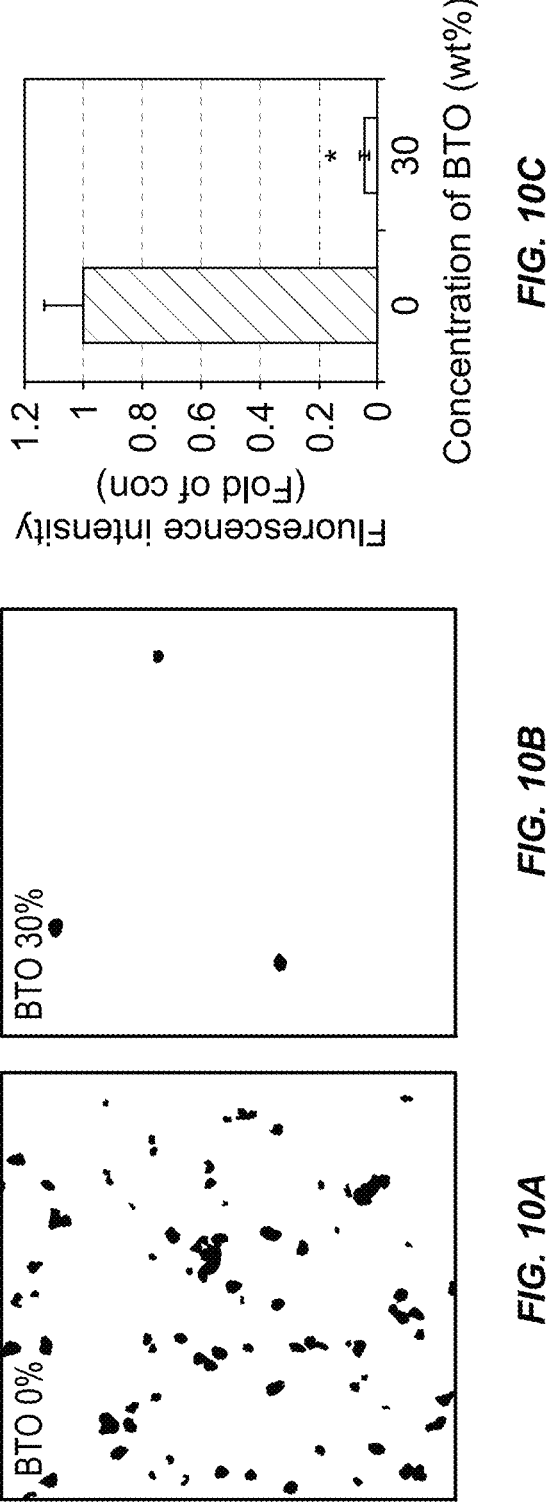
FIGS. 10A-10C illustrates the anti-biofilm activity of piezoelectric nanoparticles in accordance with some embodiments of the disclosed subject matter.

FIGS. 10A-10C illustrates the antibiofilm activity of piezoelectric nanoparticles in accordance with some embodiments of the disclosed subject matter. Repelling microbial adhesion and blocking subsequent colonization on the crown surface can be critical to minimize bacterial challenge to human gingival keratinocytes ("HGKs"), thereby reducing the prevalence of pathogenesis of peri-implant diseases. FIG. 10 depicts the anti-biofilm activity of the BTO-NPs embedded on a dental material surface against representative oral bacteria, *Streptococcus mutans*, using an in vitro biofilm model. *S. mutans* biofilms can be cultured on saliva-coated BTO-NPs embedded disc for 19 hours.

As shown in FIG. 10A, numerous sizeable *S. mutans* colonies can be evenly distributed on the disc without BTO-NPs. As shown in FIG. 10B, BTO-NPs embedded dental material surface almost completely blocked biofilm formation (i.e., a greater than 90% reduction of biomass). Collectively, the data in FIG. 10C shows the potent antibiofilm effect of BTO-NPs, which can reduce the inflammation against bacterial invasion, thereby enhancing the immunity of HGKs significantly.

Figure 11:
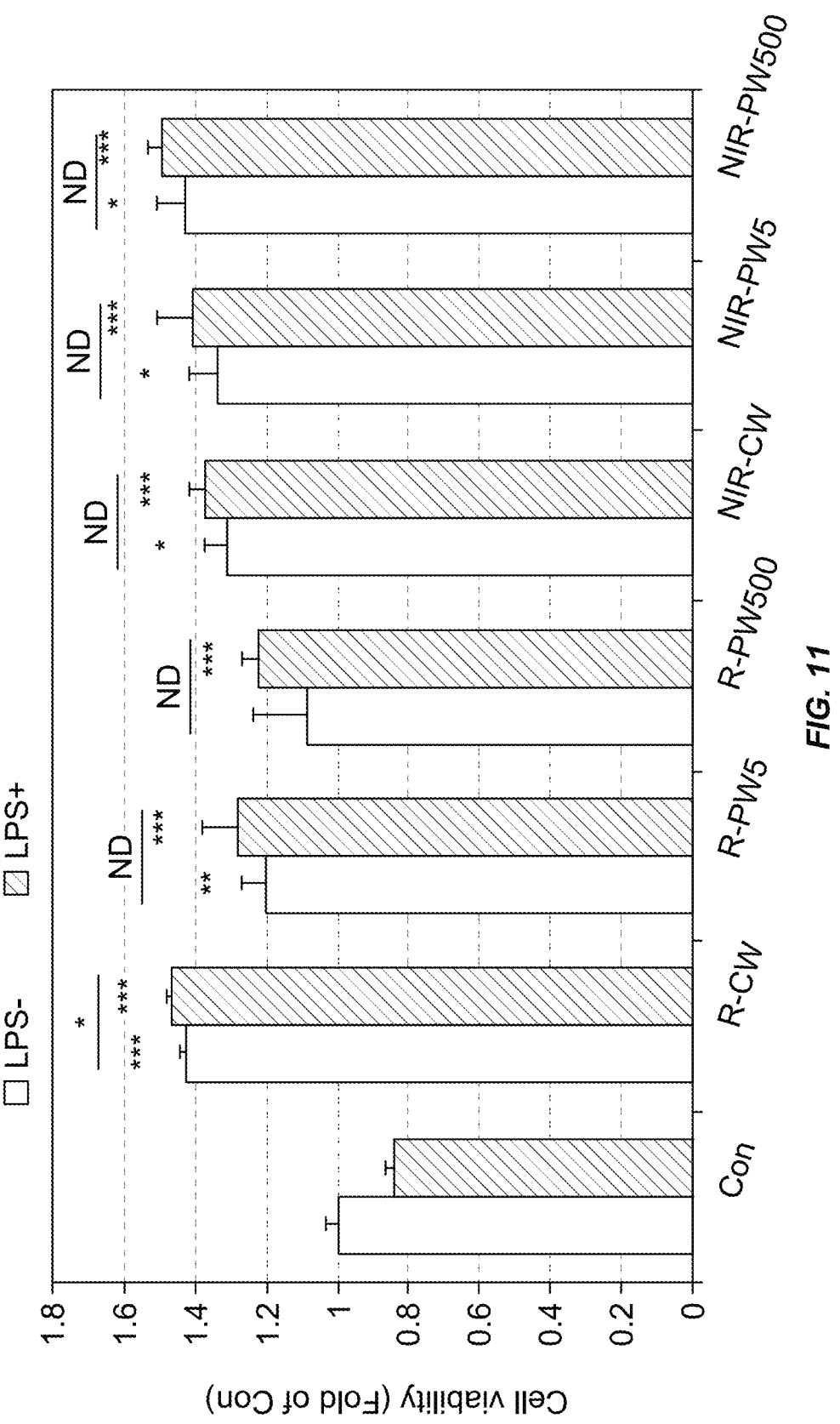
FIG. 11 illustrates the viability of human gingival keratinocytes with and without photobiomodulation in accordance with some embodiments of the disclosed subject matter.

FIG. 11 illustrates the viability of HGKs with and without PBM therapy. The efficiency of PBM therapy can be examined based on the viability of HGKs from bacterial invasion using red ("R") and near-infrared ("NIR") irradiation under the chewing motion. Continuous and pulse wave conditions (5 Hz and PW₅ or 500 Hz and PW₅₀₀, respectively) can be tested. First, Lipopolysaccharides ("LPS"), which can be the major virulent component of the outer membrane of Gram-negative bacteria that stimulates host cells and induce cell inflammation, induced inflammation on HGKs. The efficacy of the PBM therapy on LPS-inflamed HGKs cells can be tested under two parameters: 1) 90 minutes of R and NIR exposure time assuming the daily human oral motion activity; and 2) 10 μg/mL of LPS due to inflammation initiation without severe cell death. Note that blue and green irradiance can be excluded because they substantially lowered the cell viability.

HGKs can be cultured in a KGM-2 growth medium supplemented with human keratinocyte growth supplements (Lonza, Walkersville, MD), including standard insulin (8.6× 10-7 M) at 37° C. in a humid atmosphere of 5% $CO_2$. Initially, HGKs cells can be seeded at 5×10⁴ cells/well in 24-well plates and grown for 48 h at 37° C. After 48 h of incubation, cells can be washed with 1×PBS and incubated in a medium without human keratinocyte growth supplements for an additional 48 h after relevant treatments (LED irradiation and/or LPS treatment). Cell viability can be determined using MTT (3-(4,5-Dimethylthiazol-2-yl)-2,5-diphenyltetrazolium bromide) (Cell proliferation kit I, Roche, Germany). 50 μL of the MTT labeling reagent (final concentration of 0.5 mg/mL) can be added to each well. Then, the cells can be incubated in a $CO_2$ incubator at 37° C. for 4 h. 500 μL of the Solubilization buffer (10% SDS in 0.01 M HCl) can be added, and the plate can be allowed to stand overnight in the incubator to solubilize the formazan crystals. The optical density (OD) values of samples can be then measured at a wavelength of 570 nm with a microplate reader (BioTek, Winooski, VT). OD values of the treatment groups can be always normalized to that of the untreated control group.

To investigate the cell response to bacterially induced inflammation, the cells can be exposed to LPS (Sigma, St. Louis, MO). First, the optimal concentration of LPS for inflammation induction can be determined by adding various concentrations of LPS (0-100 μg/mL). After HGKs cells can be grown for 48 h, the cells can be washed and the culture medium can be replaced with fresh media (without growth supplements). Then, LPS can be added, and the cells can be subsequently incubated for an additional 48 h. With a pre-determined optimal concentration of LPS (0-20 μg/mL), the cells can be pre-treated with LEDs before LPS exposure, and the cells can be subsequently incubated for an additional 48 h. Then, the viability of cells can be evaluated using MTT assay.

The data in FIG. 11 shows that all conditions can be able to not only fully recover the viability of HGKs against LPS stimulus (vs. control with LPS), but also significantly increase the cell viability (vs. control without LPS). Interestingly, different levels of treatment efficacies under different conditions can be observed (i.e., up to 85% increase of cell viability from R-CW or NIR-PW₅₀₀ vs control with LPS), which indicates that specific wavelength or frequency can stimulate chromophore in HGKs in a different way.

Figure 12:
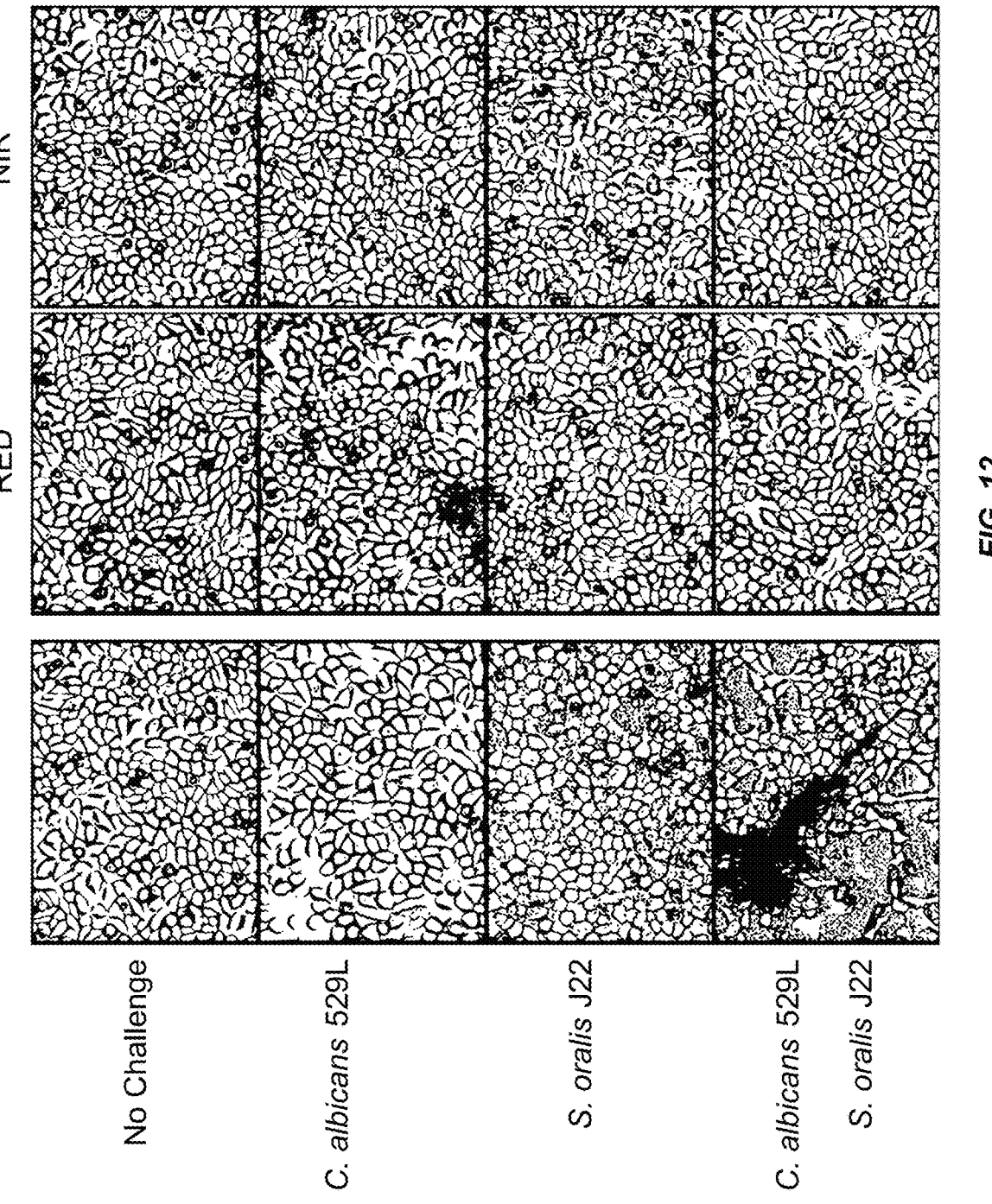
FIG. 12 shows cell responses to pathogenic microbial cells in accordance with some embodiments of the disclosed subject matter.

FIG. 12 shows cell responses to pathogenic microbial cells. To investigate the cell response to pathogenic microbial cells, a fungus *Candida albicans* and a bacterium *Streptococcus oralis* can be introduced to HGKs. The data in FIG. 12 shows that red or near-infrared irradiation can fully recover the confluency of HGKs against pathogenic microbial invasion. When there is no microbial challenge, cells can show high confluency and tight junctions between cells. Tight junctions are intercellular adhesion complexes in epithelia. Tight junctions can seal adjacent epithelial cells in a narrow band just beneath their apical surface and support the maintenance of cell polarity by restricting intermixing of apical and basolateral transmembrane components. When HGKs are exposed to a bacterium or a fungus, it shows a loss of proliferation and tight junctions. In non-limiting embodiments, when they are faced with co-infection by bacterium and fungus, tissues can be severely destroyed. However, these are almost fully recovered when HGKs can be exposed to red or infrared irradiation. In some embodiments, NIR irradiation can improve the proliferation of HGKs against microbial challenge, which can be a synergistic bacterial-fungal combined invasion. Therefore, the data revealed that the disclosed PBM therapy can recover human keratinocytes from microbial infections.

Figure 13:
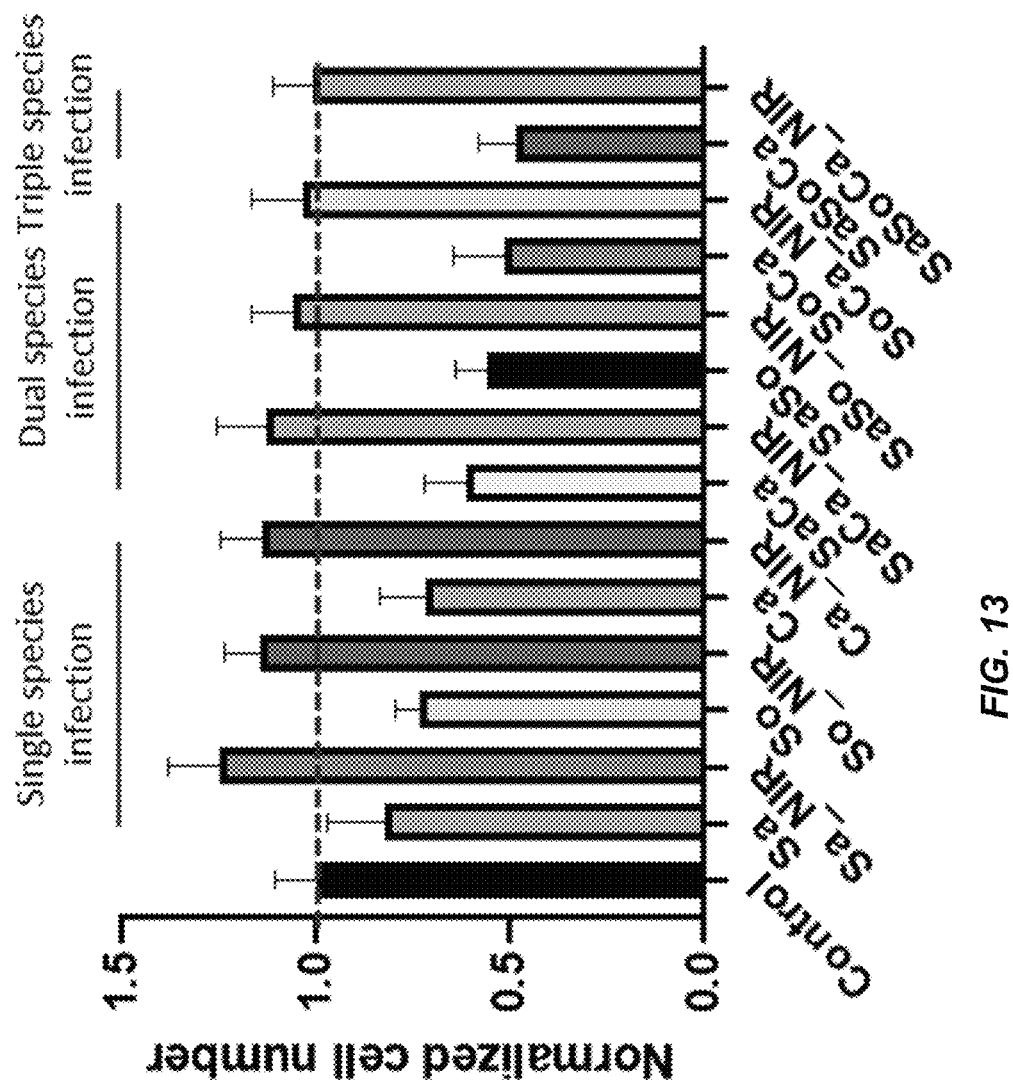
FIG. 13 shows the number of the primary human gingival keratinocytes (HGKs) after the microbial invasion with or without near-infrared (NIR) irradiation in accordance with some embodiments of the disclosed subject matter.

The data in FIG. 13 shows the number of HGKs after the microbial invasion with or without NIR irradiation. When HGKs can be infected by the bacterium *Staphylococcus aureus* (Sa) or *Streptococcus oralis* (So) or fungus *Candida albicans* (Ca) or their combination for 24 h, the HGKs number can be reduced (e.g., dual and triple-species infections). In marked contrast, the number of HGKs can be fully recovered when stimulated by NIR light, comparable to the level of cells without infection (dotted line). The data support the potent efficacy of the disclosed PBM therapy in enhancing cellular immunity against dire and abiding microbial attacks.

Figure 14:
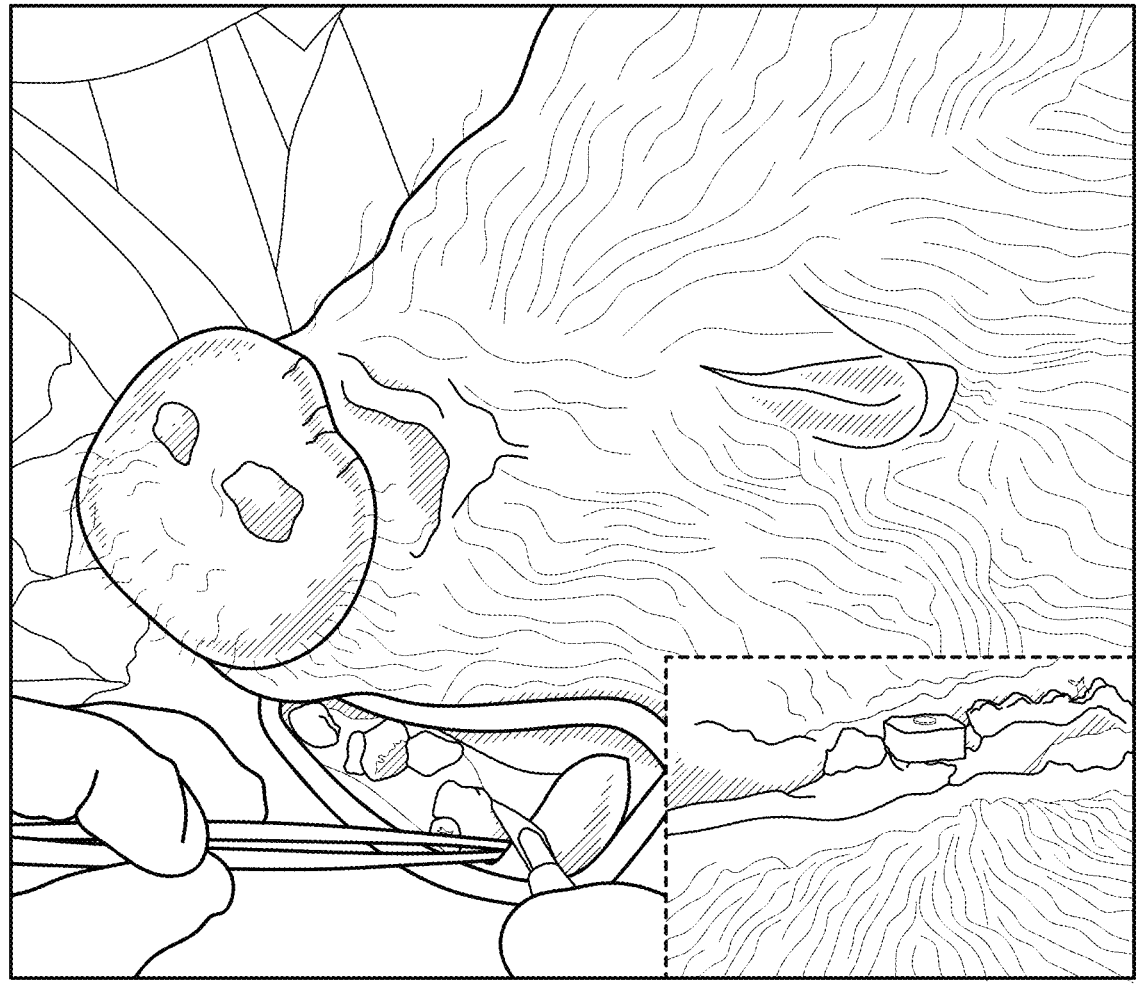
FIG. 14 shows an example SDI implanted in the mouth of a minipig in accordance with some embodiments of the disclosed subject matter.

To validate the feasibility of our device, the SDI can be installed in the mouth of a minipig. A minipig model can be used due to remarkable anatomical similarities to humans and an established periodontal disease model with varying degrees. As shown in FIG. 14, a successful surgical protocol can be laid out, and the functionality of the prototype of the SDI system can be validated using the disclosed minipig model of peri-implant diseases. For example, Minipigs, free of periodontal disease, 3-4 months of age, and an average weight of 30 kg can be used. Under the sterile conditions using an accepted general anesthesia protocol, a surgical extraction of mandibular premolars and/or the first molar can be performed. After the surgical extraction of the mandibular premolar and/or the first molar, the alveolar bone can be prepared for titanium implants, which can be placed in each hemimandible. Then, soft tissues can be closed, allowing the construct to be healed. Approximately six weeks later, the animals can be anesthetized for placement of the Smart Crown and Smart Abutment on the integrated implants. The disclosed protocol can be used in the dental clinic.

The results from independent experiments can be expressed as mean±SD. The statistical analysis of the experimental data can be performed using the Student's t-test. Experiments can be repeated at least twice for assays. Data can be considered statistically significant when P-value less than 0.01.

The foregoing merely illustrates the principles of the disclosed subject matter. Various modifications and alterations to the described embodiments will be apparent to those skilled in the art in view of the teachings herein. It will thus be appreciated that those skilled in the art will be able to devise numerous techniques which, although not explicitly described herein, embody the principles of the disclosed subject matter and are thus within its spirit and scope.

The invention claimed is:

1. A smart dental implant system for ambulatory dental care of a patient, comprising:
   a crown, adapted to mimic a patient's anatomy and location of the smart dental implant system, further comprising piezoelectric nanoparticles, disposed on a surface of the crown, wherein the piezoelectric nanoparticles are adapted to generate electricity from oral motion of the patient, wherein the oral motion includes one or more of chewing, biting, and brushing; and
   an abutment, coupled to the crown, further comprising:
      an energy harvesting circuit, operationally coupled to the piezoelectric nanoparticles, adapted to harvest the electricity; and
      a micro LED array, operationally coupled to the energy harvesting circuit, wherein the micro LED array is adapted to photobiomodulate surrounding peri-implant soft tissue.

2. The smart dental implant system of claim 1, further comprising a metal post, adapted for insertion into a jawbone of the patient, and a retaining screw, adapted to couple the metal post to the abutment.

3. The smart dental implant system of claim 1, wherein the piezoelectric nanoparticles are disposed in a dental material on the surface of the crown.

4. The smart dental implant system of claim 3, wherein the piezoelectric nanoparticles are barium titanate nanoparticles.

5. The smart dental implant system of claim 4, wherein the barium titanate nanoparticles are disposed in the dental material at a concentration of between 1% and 40% by weight.

6. The smart dental implant system of claim 4, wherein the barium titanate nanoparticles are infused with a ceramic dental material by a sintering process.

7. The smart dental implant system of claim 1, wherein the piezoelectric nanoparticles are further adapted to have an anti-biofilm effect.

8. The smart dental implant system of claim 1, wherein the energy harvesting circuit further comprises an AC-to-DC rectifier, adapted to convert the electricity into a DC voltage, and a power management unit, adapted to store the DC voltage.

9. The smart dental implant of system of claim 1, wherein the abutment further comprises an LED driver circuit, adapted to generate two different voltage levels and frequencies such that the micro LED array is adapted to photobiomodulate surrounding peri-implant soft tissue at multiple wavelengths.

10. The smart dental implant system of claim 1, wherein the micro LED array further comprises at least four micro LED disposed, disposed 90 degrees apart, such that the micro LED array is adapted to photobiomodulate surrounding peri-implant soft tissue.

11. The smart dental implant system of claim 1, wherein the crown is further adapted to have sufficient mechanical strength to withstand large biting forces by a two-phase composite configuration.

12. A method of promoting healthy tissue and preventing bone loss at an interface of a dental implant and soft tissue of a patient, comprising:
   inserting a metal post into a jawbone of the patient;
   coupling a dental implant to the metal post, wherein piezoelectric nanoparticles are disposed on a surface of the dental implant such that the piezoelectric nanoparticles generate electricity from oral motion of the patient, wherein the oral motion includes one or more of chewing, biting, and brushing;

harvesting the electricity from the piezoelectric nanoparticles as harvested electricity; and photobiomodulating surrounding peri-implant soft tissue with the harvested electricity.

13. The method of claim 12, wherein the dental implant is coupled to the metal post with a retaining screw.

14. The method of claim 11, wherein the harvesting includes converting the electricity into a DC voltage and storing the DC voltage as the harvested electricity.

15. The method of claim 11, further comprising fusing the piezoelectric nanoparticles to a dental material to create the dental implant.

16. The method of claim 15, wherein the piezoelectric nanoparticles are barium titanate nanoparticles.

17. The method of claim 16, wherein the barium titanate nanoparticles are disposed in the dental material on the surface of the dental implant at a concentration of between 1% and 40% by weight.

18. The method of claim 16, wherein the barium titanate nanoparticles are infused in the dental material as a bulk material by a sintering process.

19. The method of claim 12, wherein the piezoelectric nanoparticles repel biofilm adhesion and block subsequent biofilm colonization on the dental implant.

20. The method of claim 12, wherein the photobiomodulating includes multiple wavelengths.

\* \* \* \* \*